(12) United States Patent
Alkhabbaz et al.

(10) Patent No.: US 10,557,730 B2
(45) Date of Patent: Feb. 11, 2020

(54) ALTERNATING MAGNETIC FIELD FLOW METERS WITH EMBEDDED QUALITY ASSURANCE AND CONTROL

(71) Applicant: Saudi Arabian Oil Company, Dhahran (SA)

(72) Inventors: Fouad M. Alkhabbaz, Qatif (SA); Maatoug Al-Maatoug, Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/447,269

(22) Filed: Jun. 20, 2019

(65) Prior Publication Data

US 2019/0301904 A1    Oct. 3, 2019

Related U.S. Application Data

(63) Continuation-in-part of application No. 15/630,736, filed on Jun. 22, 2017, now Pat. No. 10,330,511.

(51) Int. Cl.
| | |
|---|---|
| *G01F 1/58* | (2006.01) |
| *G01F 15/02* | (2006.01) |
| *G01N 27/10* | (2006.01) |
| *H01F 7/20* | (2006.01) |

(52) U.S. Cl.
CPC .............. *G01F 1/586* (2013.01); *G01F 1/584* (2013.01); *G01F 15/024* (2013.01); *G01N 27/10* (2013.01); *H01F 7/20* (2013.01)

(58) Field of Classification Search
CPC .................................. G01F 1/58; G01F 15/02
See application file for complete search history.

(56) References Cited

U.S. PATENT DOCUMENTS

| | | | |
|---|---|---|---|
| 3,104,549 A | 9/1963 | Humbert et al. | |
| 3,316,767 A | 5/1967 | Liebert | |
| 3,373,608 A | 3/1968 | Ketelsen | |
| 4,051,723 A | 10/1977 | Head et al. | |

(Continued)

FOREIGN PATENT DOCUMENTS

| | | |
|---|---|---|
| EP | 770856 | 9/2003 |
| GB | 1493527 | 11/1977 |

OTHER PUBLICATIONS

International Search Report and Written Opinion issued in International Application No. PCT/US2018/037252 dated Sep. 19, 2018, 16 pages.

*Primary Examiner* — Jewel V Dowtin
(74) *Attorney, Agent, or Firm* — Fish & Richardson P.C.

(57) ABSTRACT

A method of characterizing a fluid flow by an alternating magnetic field flow meter, comprising determining a flow rate of a fluid flowing through a conduit by generating a first magnetic field to move a magnetic token along a direction of a flow path of a fluid flowing through a conduit, detecting a first electrical signal based on the movement of the magnetic token, generating a second magnetic field to move the magnetic token opposite to the direction of the flow path, detecting a second electrical signal based on the movement of the magnetic token, and determining a conductivity of the fluid flowing through the conduit by generating a current along the flow path and detecting a third electrical signal based on the current generated along the flow path, and determining a conductivity measurement of the fluid flow based on the detected third electrical signal.

23 Claims, 13 Drawing Sheets

(56) References Cited

U.S. PATENT DOCUMENTS

| | | | |
|---|---|---|---|
| RE31,186 E | | 3/1983 | Rosenweig |
| 4,517,846 A | | 5/1985 | Harrison et al. |
| 4,777,833 A | | 10/1988 | Carpenter |
| 4,901,018 A | | 2/1990 | Lew |
| 5,090,250 A | | 2/1992 | Wada |
| 5,392,648 A | | 2/1995 | Robertson |
| 5,417,118 A | | 5/1995 | Lew et al. |
| 6,006,831 A | | 12/1999 | Schlemmer et al. |
| 6,085,599 A | | 7/2000 | Feller |
| 6,237,424 B1 | | 5/2001 | Salmasi et al. |
| 6,463,807 B1 | | 10/2002 | Feller |
| 6,626,048 B1 | | 8/2003 | Dam Es et al. |
| 6,920,799 B1 | | 7/2005 | Schulz |
| 7,265,544 B2 | * | 9/2007 | Keese ................... G01F 1/60 324/306 |
| 7,540,202 B2 | | 6/2009 | Bier |
| 7,574,907 B2 | | 8/2009 | Maute |
| 8,051,722 B2 | | 11/2011 | Voigt et al. |
| 8,365,612 B2 | * | 2/2013 | Izumi ................... G01F 1/584 277/637 |
| 8,875,379 B2 | | 11/2014 | Maute |
| 2004/0045368 A1 | | 3/2004 | Schoeb |
| 2005/0193832 A1 | | 9/2005 | Tombs et al. |
| 2007/0163359 A1 | * | 7/2007 | Nielsen ................ G01F 1/584 73/861.12 |
| 2013/0085687 A1 | | 4/2013 | Danov et al. |
| 2014/0342373 A1 | | 11/2014 | Viovy et al. |

\* cited by examiner

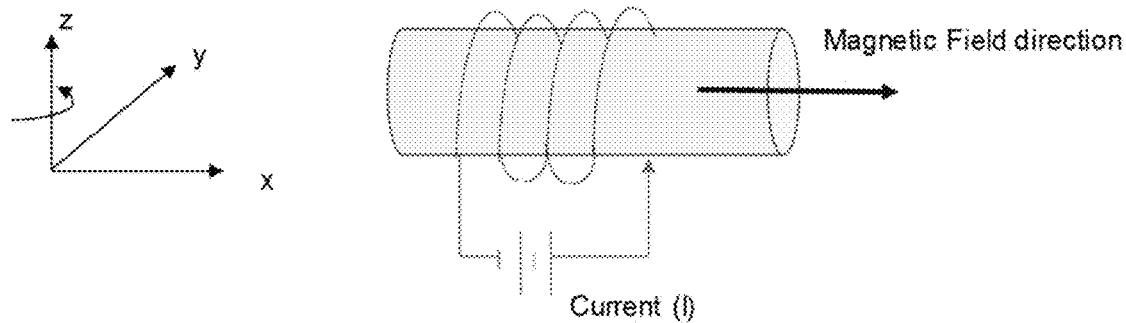
FIG. 3
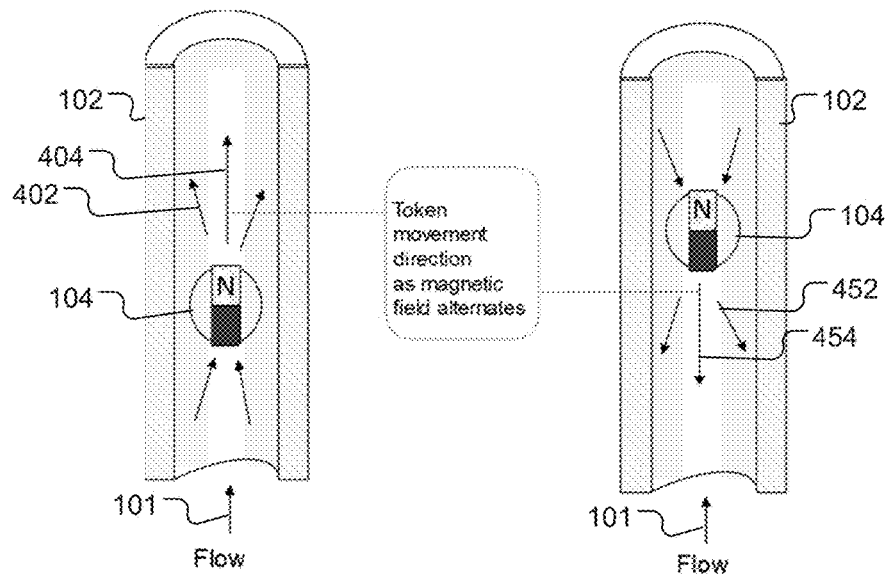
FIG. 4A  FIG. 4B

ALTERNATING MAGNETIC FIELD FLOW METERS WITH EMBEDDED QUALITY ASSURANCE AND CONTROL

CROSS REFERENCE TO RELATED APPLICATIONS

This application is a Continuation-in-Part of U.S. patent application Ser. No. 15/630,736, filed Jun. 22, 2017, the entire contents of which are incorporated herein by reference.

TECHNICAL FIELD

This specification relates to flow meters, particularly to magnetic flow meters for fluid flow measurements.

BACKGROUND

An electromagnetic flow meter can be used to measure a flow of an electrically conductive fluid along a flow path in a conduit. The electromagnetic flow meter makes use of electrodynamic induction and is operative to apply a magnetic field across the flow path. Charge carriers in the conductive fluid moved perpendicularly to the magnetic field causes the induction of a voltage across the conductive fluid. As the conductive fluid can conduct electricity, the induced voltage can be measured by electrodes arranged essentially perpendicular to the flow direction of the fluid and the magnetic field, for example, on both ends of the conduit. The voltage induced in the electrodes is proportional to the velocity of the fluid flow averaged over a cross section of the conduit, and accordingly proportional to the volume flow rate or massive flow rate of the fluid flow. However, such electromagnetic flow meter cannot measure non-conductive fluids.

SUMMARY

The present specification describes methods, apparatus, and systems for providing fluid flow measurements by utilizing a velocity variance of a free moving magnet in an alternating magnetic field. This technology can be used for both conductive fluids and non-conductive fluids.

The specification further describes providing alternating magnetic field flow measurement with embedded quality assurance and control, by enabling distributed fluid salinity measurements, determination and control as part of integrated community of flow meters that can be used to measure the flow and quality of fluids in Supervisory Control and Data Acquisition (SCADA) systems for upstream oil and gas applications, pipeline applications, water and utility applications and can provide community-control of variable salinity of fluid output for a variety of applications and manufacturing products lines.

One aspect of the present disclosure features an alternating magnetic field flow meter including: a magnetic token movable within a conduit operable to guide a fluid flow along a flow path; a magnetic field generator configured to: generate a first magnetic field to move the magnetic token along a direction of the flow path, and generate a second magnetic field to move the magnetic token opposite to the direction of the flow path; and a detector configured to detect: a first electrical signal associated with the movement of the magnetic token along the direction of the flow path, and a second electrical signal associated with the movement of the magnetic token opposite to the direction of the flow path, where a flow rate of the fluid flow is determined based on the detected first electrical signal and the detected second electrical signal.

In some implementations, the detector includes a piezoelectric sensor including a first surface coupled to an inlet of the conduit and a second surface coupled to an outlet of the conduit, and the detector is configured to: detect a first voltage signal when the magnetic token is moved to deform the second surface along the direction of the flow path, the first electrical signal including the first voltage signal; and detect a second voltage signal when the magnetic token is moved to deform the first surface opposite to the direction of the flow path, the second electrical signal including the second voltage signal.

The magnetic field generator can include an electromagnetic coil and is configured to: generate the first magnetic field by inputting a current into the electromagnetic coil, and generate the second magnetic field by reversing a polarity of the current into the electromagnetic coil.

In some implementations, the detector includes a current detector with a first electrode coupled to a first end of the electromagnetic coil and a second electrode coupled to a second end of the electromagnetic coil, and the magnetic field generator is configured to: generate the first magnetic field to move the magnetic token along the direction of the flow path for a first period of time and then de-energize the first magnetic field, such that the current detector receives a first current signal in response to the magnetic token moving in the electromagnetic coil without the first magnetic field and along the direction of flow path, the first electrical signal including the first current signal, and generate the second magnetic field to move the magnetic token opposite to the direction of the flow path for a second period of time and then de-energize the second magnetic field, such that the current detector receives a second current signal in response to the magnetic token moving in the electromagnetic coil without the second magnetic field and opposite to the direction of flow path, the second electrical signal including the second voltage signal.

The magnetic field generator can be configured to alternately generate the first magnetic field and the second magnetic field, and the detector can be configured to detect a plurality of first electrical signals and corresponding second electrical signals when the magnetic token is moved within the conduit by the alternating first magnetic field and second magnetic field, and the flow rate of the fluid flow can be determined based on respective differences between the first electrical signals and corresponding second electrical signals.

The alternating magnetic field flow meter can be configured to: determine a difference between the first electrical signal and the second electrical signal; and determine the flow rate of the fluid flow based on the determined difference and associations between differences of electrical signals and respective flow rates. The fluid flow can include at least one of a conductive material or a non-conductive material.

In some implementations, a frequency of switching the current polarity is configurable to allow for manual or automatic adjustment of the flow meter's performance in accordance to special environment conditions. The frequency of the switching current polarity and the meter's accuracy can be directly proportional to each other. For example, in environments or operational conditions where a flow is more constant than others, the current polarity can be switched less frequently to determine an accurate flow rate. In other environments where a flow is more dynamic, a higher frequency of switching the current polarity can be used to provide a higher accuracy flow measurement.

In some implementations, the alternating magnetic field flow meter further includes a calibrator configured to automatically calibrate the flow rate with a correction factor. In some cases, the correction factor is obtained based on a contaminant distribution pattern for the fluid flow and associations between fluid flows with known contaminant distribution patterns and corresponding correction factors. In some cases, the calibrator is configured to generate the correction factor based on a predicted contaminant distribution pattern for the fluid flow and accumulated calibration information including contaminant distribution patterns and associated accuracy variances of flow meters.

Another aspect of the present disclosure features a method of measuring a flow rate of a fluid flow by an alternating magnetic field flow meter. The method includes: generating a first magnetic field to move a magnetic token along a direction of a flow path of a fluid flowing through a conduit; detecting a first electrical signal based on the movement of the magnetic token along the direction of the flow path; generating a second magnetic field to move the magnetic token opposite to the direction of the flow path; detecting a second electrical signal based on the movement of the magnetic token opposite to the direction of the flow path; and determining the flow rate of the fluid flow based on the detected first electrical signal and the detected second electrical signal.

In some implementations, detecting a first electrical signal includes detecting a first voltage signal when the magnetic token is moved to deform a first surface of a piezoelectric sensor coupled to an outlet of the conduit, and detecting a second electrical signal includes detecting a second voltage signal when the magnetic token is moved to deform a second surface of the piezoelectric sensor coupled to an inlet of the conduit.

In some implementations, generating the first magnetic field includes inputting a current into an electromagnetic coil, and generating the second magnetic field includes reversing a polarity of the current into the electromagnetic coil.

In some implementations, the method further includes: after generating the first magnetic field for a first period of time, de-energizing the first magnetic field, such that the magnetic token moves in the electromagnetic coil without the first magnetic field and along the direction of flow path to generate a first current signal, where detecting a first electrical signal includes detecting the first current signal; and, after generating the second magnetic field for a second period of time, de-energizing the second magnetic field, such that the magnetic token moves in the electromagnetic coil without the second magnetic field and opposite to the direction of flow path to generate a second current signal, where detecting a second electrical signal includes detecting the second current signal.

Determining the flow rate of the fluid flow can include: calculating a difference between the first electrical signal and the second electrical signal; and determining the flow rate based on the calculated difference and associations between differences of electrical signals and respective flow rates.

In some implementations, the method includes: alternately generating the first magnetic field and the second magnetic field; detecting a plurality of first electrical signals and a plurality of corresponding second electrical signals; and determining the flow rate of the fluid flow based on respective differences between the first electrical signals and corresponding second electrical signals.

In some implementations, the method further includes: obtaining a correction factor based on a contaminant distribution pattern for the fluid flow and associations between fluid flows with known contaminant distribution patterns and corresponding correction factors; and calibrating the flow rate with the correction factor. The method can further include: generating a correction factor based on a predicted contaminant distribution pattern for the fluid flow and accumulated calibration information including contaminant distribution patterns and associated accuracy variances of flow meters; and calibrating the flow rate with the correction factor.

A further aspect of the present disclosure features an alternating magnetic field flow meter apparatus including: a magnetic token movable within a conduit configured to guide a hydrocarbon flow along a flow path; a magnetic field generator configured to generate alternating magnetic fields within the conduit to move the magnetic token along the flow path with a first flow velocity and opposite to the flow path with a second flow velocity; a detector configured to measure respective first and second electrical signals responsive to the alternating magnetic fields, the first and second electrical signals associated with the first and second flow velocities; and a processor configured to determine a flow rate of the hydrocarbon flow based on the first and second electrical signals.

The alternating magnetic field flow meter apparatus can further include a calibrator configured to automatically calibrate the flow rate with a correction factor.

In some implementations, the calibrator is configured to determine the correction factor based on calibration information including at least one of: contaminants known with even distribution patterns and corresponding correction factors, performance curves representing relations between flow rates and one or more process variables including temperature, density, pressure, or viscosity, one or more lab-based calibration tables, a theoretical calibration or a modeling simulation, or empirical field testing results from flow meters under a same environment as the hydrocarbon flow.

In some implementations, the calibrator is configured to: predict, by at least one of a fuzzy logic or a neural network, one or more performance-affecting parameters for the hydrocarbon flow based on accumulated calibration information of flow meters, and generate the correction factor based on the predicted performance-affecting parameters.

In some implementations, the calibrator is configured to: update an operating condition through measurements of a plurality of process variables, provide a real-time estimation of one or more unmeasured properties of the hydrocarbon flow based on the updated process variables, and generate the correction factor based on the real-time estimation of the one or more unmeasured properties.

In some implementations, the alternating magnetic field flow meter apparatus further includes a communication module configured to communicate calibration information with one or more other flow meters via inter-meter communication, and the calibrator is configured to determine the correction factor based on the calibration information from the one or more other flow meters.

In some implementations, the calibrator comprises an on-board voting module configured to: transmit a measurement output of the flow rate to a voting server configured to communicate with a plurality of flow meters, fluid flows measured by the plurality of flow meters having a similar condition environment as the hydrocarbon flow, receive from the voting server a meter factor indicating that the measurement output of the flow rate is outside a majority vote among measurement outputs of the plurality of flow meters, and determine the correction factor based on the meter factor, such that the measurement output of the flow rate calibrated with the determined correction factor is inside the majority vote.

In some implementations, the calibrator is configured to: transmit a measurement output of the flow rate to a control server configured to communicate with a plurality of flow meters, fluid flows measured by the plurality of flow meters having a diverse condition environment as the hydrocarbon flow, receive from the control server a meter factor indicating that the measurement output of the flow rate is off a normalization curve among measurement outputs of particular flow meters of the plurality of flow meters, fluid flow measured by the particular flow meters having a similar condition environment as the hydrocarbon flow, and determine the correction factor based on the meter factor, such that the measurement output of the flow rate calibrated with the determined correction factor is on the normalization curve.

Another aspect of the present disclosure features a method of characterizing a fluid flow by an alternating magnetic field flow meter, the method comprising determining a flow rate of a fluid flowing through a conduit by generating a first magnetic field to move a magnetic token along a direction of a flow path of a fluid flowing through a conduit, detecting a first electrical signal based on the movement of the magnetic token along the direction of the flow path, generating a second magnetic field to move the magnetic token opposite to the direction of the flow path, detecting a second electrical signal based on the movement of the magnetic token opposite to the direction of the flow path, and determining the flow rate of the fluid flow based on the detected first electrical signal and the detected second electrical signal, and determining a conductivity of the fluid flowing through the conduit by generating a current along the flow path of the fluid flowing through the conduit detecting a third electrical signal based on the current generated along the flow path, and determining a conductivity measurement of the fluid flow based on the detected third electrical signal.

In some implementations, the method includes after generating the first magnetic field for a first period of time, de-energizing the first magnetic field, after generating the second magnetic field for a second period of time, de-energizing the second magnetic field, and after generating the current for a third period of time, de-energizing a charge emitter generating the current. It can further include sequentially generating the first magnetic field, the second magnetic field, and the current, detecting a plurality of first electrical signals, a plurality of corresponding second electrical signals, and a plurality of third electrical signals, and synchronizing determination of the flow rate of the fluid flow based on respective differences between the first electrical signals and corresponding second electrical signals and the conductivity measurement based on the plurality of third signals.

The conductivity measurement can be a total dissolved solids level. The method can include obtaining a salinity factor based on the third electrical signal, or determining additional fluid properties based on the salinity factor. The fluid properties are fluid density and temperature.

Another aspect of the present disclosure is a method of characterizing fluid flows by a network of alternating magnetic field flow meters, comprising at each flow meter, determining a flow rate of a fluid flowing through a respective conduit by generating a first magnetic field to move a magnetic token along a direction of a flow path of a fluid flowing through the respective conduit, detecting a first electrical signal based on the movement of the magnetic token along the direction of the flow path, generating a second magnetic field to move the magnetic token opposite to the direction of the flow path, detecting a second electrical signal based on the movement of the magnetic token opposite to the direction of the flow path, and determining the flow rate of the fluid flow based on the detected first electrical signal and the detected second electrical signal, at each flow meter, determining a conductivity of the fluid flowing through the respective conduit by generating a current along the flow path of the fluid flowing through the conduit, detecting a third electrical signal based on the current generated along the flow path, and determining a conductivity measurement of the fluid flow based on the detected third electrical signal, receiving, at a first flow meter, information about the conductivity measurement determined by a second flow meter in the network, and modifying the conductivity measurement of the first flow meter using the received information.

In some implementations, the method includes determining a plurality of conductivity measurements over time for one of the flow meters on the network, and storing the plurality of conductivity measurements, and generating a salinity factor for the flow meter based on the plurality of conductivity measurements. In some implementations, the method includes generating trend data based on the conductivity measurements. Or, after generating the first magnetic field for a first period of time, de-energizing the first magnetic field, after generating the second magnetic field for a second period of time, de-energizing the second magnetic field, and after generating the current for a third period of time, de-energizing a charge emitter generating the current. Or, sequentially generating the first magnetic field, the second magnetic field, and the current, detecting a plurality of first electrical signals, a plurality of corresponding second electrical signals, and a plurality of third electrical signals, and synchronizing determination of the flow rate of the fluid flow based on respective differences between the first electrical signals and corresponding second electrical signals and the conductivity measurement based on the plurality of third signals. The conductivity measurement is a total dissolved salts level. The method can include obtaining a salinity factor based on the third electrical signal, or determining additional fluid properties based on the salinity factor. The fluid properties are fluid density and temperature.

Another aspect of the present disclosure is an alternating magnetic field flow apparatus comprising a magnetic token movable within a conduit configured to guide a hydrocarbon flow along a flow path, a magnetic field generator configured to generate alternating magnetic fields within the conduit to move the magnetic token along the flow path with a first flow velocity and opposite to the flow path with a second flow velocity, a detector configured to measure respective first and second electrical signals responsive to the alternating magnetic fields, the first and second electrical signals associated with the first and second flow velocities, a charge emitter configured to generate a current along the flow path of the fluid flowing through the conduit, a current meter configured to measure current signals resulting from generating the current along the flow path, and a processor configured to determine a flow rate of the hydrocarbon flow based on the first and second electrical signals and determine a salinity factor of the hydrocarbon flow based on the current signals.

In some implementations, the apparatus includes a communication module configured to communicate salinity factor information with one or more other flow meters via inter-meter communication, wherein the processor is configured to modify the salinity factor based on the salinity factor information from the one or more other flow meters. The apparatus comprises a piezoelectric sensor including a first surface coupled to an inlet of the conduit and a second surface coupled to an outlet of the conduit that are configured to act as electrodes for measuring the current signals. The detector is configured to detect a first voltage signal when the magnetic token is moved to deform the second surface along the direction of the flow path, the first electrical signal including the first voltage signal, and detect a second voltage signal when the magnetic token is moved to deform the first surface opposite to the direction of the flow path, the second electrical signal including the second voltage signal. A synchronization clock is configured to control the magnetic field generator to generate the alternating magnetic fields at different times (for flow measurement) than it controls the charge emitter to generate the current (for quality assessment). The salinity factor is a measurement of a total dissolved solids level in the fluid. The salinity factor is determined by a conductivity measurement based on the current signals.

The details of one or more implementations of the subject matter of this specification are set forth in the accompanying drawings and associated description. Other features, aspects, and advantages of the subject matter will become apparent from the description, the drawings, and the claims.

DESCRIPTION OF DRAWINGS

FIG. 3 is a schematic diagram of an electromagnetic coil for magnetic field generation.

FIG. 4A shows a flow scenario where a magnetic token is moved by a magnetic field along a fluid flow.

FIG. 4B shows another flow scenario where the magnetic token is moved by a reversing magnetic field against the fluid flow.

DETAILED DESCRIPTION

Implementations of the present specification provide methods, apparatus, and systems for providing fluid flow measurements by utilizing a velocity variance of a free moving magnet in an alternating magnetic field. The free moving magnet can be placed inside a conduit, for example, a ceramic tube, where a sample is flowing through at a flow rate. The sample can include gas, liquid, slurry, or any combination thereof. The sample can include conducive materials, non-conductive material, or any combination thereof. An electromagnetic coil surrounding the conduit can be used to generate a magnetic field when energized by a current. The magnetic field can generate a magnetic force or flux along a longitudinal axis of the conduit.

When the magnetic field is energized to have a direction same as the sample flow direction, the magnet moves horizontally along the sample flow in the conduit with a flow velocity V1; when the magnetic field alternates (for example, by reversing the polarity of the input current), the magnetic force or flux of the magnetic field is opposite to the sample flow direction, and the magnet moves against the sample flow with a flow velocity V2. In some examples, the flow velocity V1 and the flow velocity V2 can be measured by a piezoelectric sensor positioned on both ends of the tube, as described below in FIG. 1. In some examples, the flow velocity V1 and the flow velocity V2 can be measured by an electric field generated by the time-varying magnetic field due to the movement of the magnet itself within the electromagnetic coil, as described below in FIG. 2.

The flow rate V of the sample in the conduit can be proportional to a difference of V1 and V2. A volumetric flow rate Q=V*A (cross-sectional area), and/or a mass flow rate M=Q*Density can be determined accordingly. The flow meter based on the alternating magnetic field can be manually or automatically calibrated by implementing a neural network logic that predicts performance-affecting contaminants, as discussed in further details in FIG. 10.

Unlike electromagnetic flow meters that require fluids to be conductive, the alternating magnetic field flow meters (or flowmeters) described herein can work for both conductive and non-conductive fluids, which enable a wide range of flow measurement applications. For example, the alternating magnetic field flow meters can be used in oil & gas processing applications, such as measuring a volume-flow or mass-flow of a hydrocarbon fluid out of a wellbore or in-plant piping. The alternating magnetic field flow meters can be automatically calibrated to achieve high and reliable detection accuracy. Note that the terms "flow meter" and "flowmeter" can be interchangeably used in the present disclosure.

Figure 1:
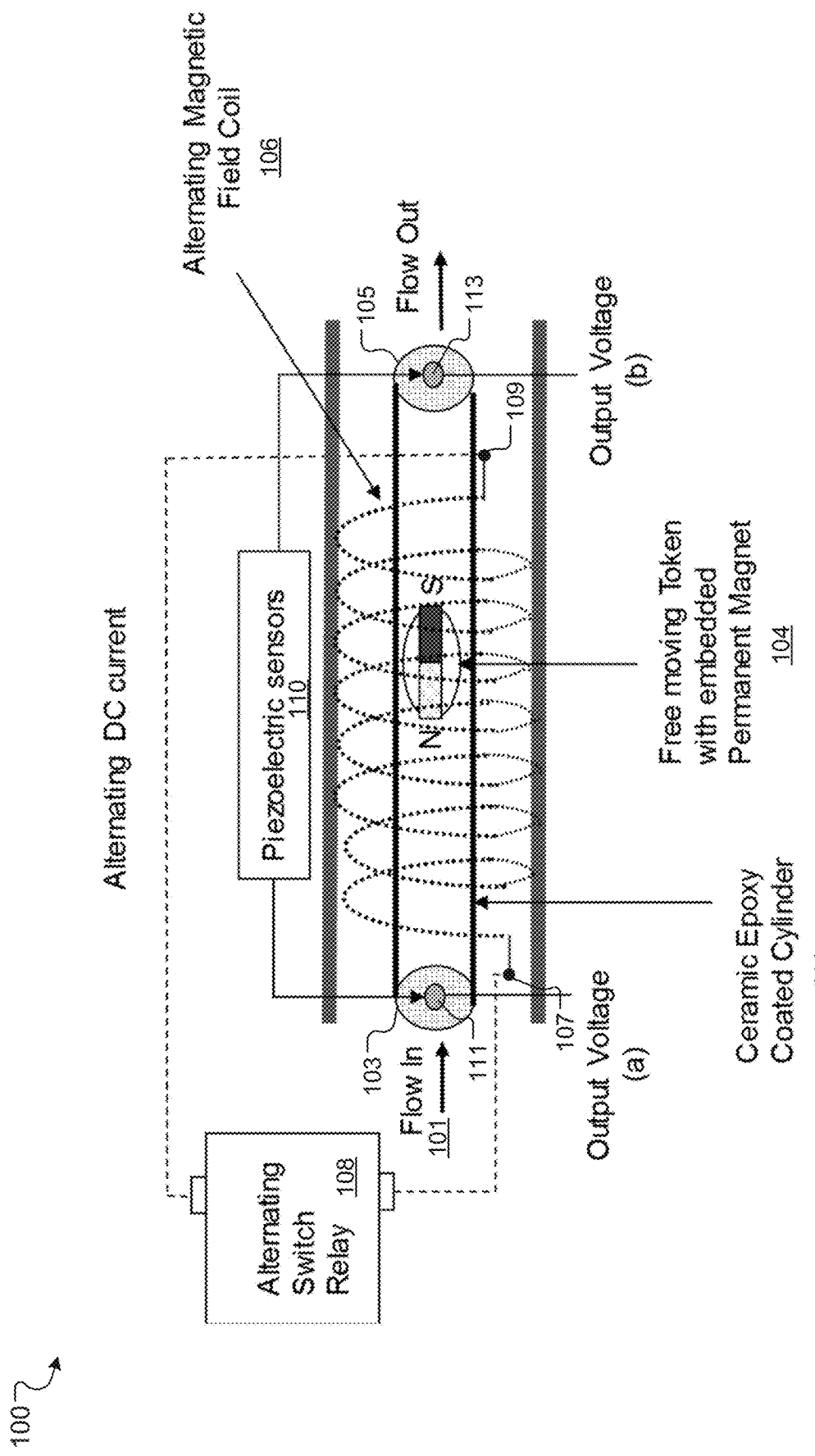
FIG. 1 is a schematic diagram of an example alternating magnetic field flow meter using a piezoelectric sensor for detection according to the present disclosure.

FIG. 1 is a schematic diagram of an example alternating magnetic field flow meter 100 according to the present disclosure. The flow meter 100 includes a conduit 102, a magnetic token 104, an electromagnetic coil 106 as a magnetic field generator, and a piezoelectric sensor 110 as a detector. The conduit 102 can include any non-corrosive and non-electrically-conductive material, for example, a ceramic material. The conduit 102 can extend along a longitudinal direction. In some examples, the conduit includes a cylindrical tube. For illustration only in FIG. 1, the conduit 102 includes a ceramic epoxy coated cylinder.

A fluid flow 101 can flow through the conduit 102 from an inlet 103 to an outlet 105, and the conduit 102 can guide the fluid flow along a flow path. A direction of the flow path can be substantially parallel to the longitudinal direction. The fluid flow can include a liquid flow, a gas flow, a slurry flow, or any combination thereof. The fluid flow can include a conductive material, a non-conductive material, or any combination thereof.

The electromagnetic coil 106 is used as a magnetic field generator. The coil 106 is configured to receive a current from a power source 108 and generate a magnetic field based on the current. The coil 106 can include a coiled wire having electrical nodes 107 and 109 on both ends. The power source 108 can include an alternating switch relay configured to alternate (or switch) a polarity (or direction) of the current so as to provide an alternating current to the coil 106. For example, the current can flow into the coil 106 from the node 107 and out from the node 109 for a period of time, and then the current is reversed to flow into the coil 106 from the node 109 and out from the node 107 for another period of time. The coil 106 can then generate an alternating magnetic field based on the alternating current.

FIG. 3 is a schematic diagram 300 showing a magnetic field generator using an electromagnetic coil, for example, the coil 106 of FIG. 1. As a DC (direct current) current moves through the coil, a magnetic field with north "N" and south "S" polar sides is generated. A direction of the generated magnetic field is determined by a "Right-Hand" rule in an x-y-z coordination system. According to the "Right-Hand" rule, the right thumb points along the 'z' axis in a positive 'z'-direction and the curl of the fingers represents a motion from the 'x' axis to the 'y' axis. When viewed from the top, the system is oriented in a counter-clockwise direction. As illustrated in FIG. 3, when the DC current flows from right to left through the coil, the direction of the generated magnetic field is along the positive 'z'-direction. When the input DC current changes the polarity, that is, the direction of the current changes from left to right through the coil, the direction of the generated magnetic field reverses, for example, along a negative 'z'-direction.

Referring back to FIG. 1, the coil 106 defines an inner space along the longitudinal direction, and the conduit 102 is arranged within the inner space of the coil 106. The direction of the generated magnetic field by the coil 106 can be also along the longitudinal direction. Thus, the direction of the flow path of the fluid flow can be substantially parallel to (or same as) the direction of the generated magnetic field. By changing a direction of the current into the coil 106, the generated magnetic field can have the same direction as the flow path or a reversed direction against the flow path.

The magnetic token 104 is movable within the conduit 102. The magnetic token 104 can have polar sides "N" and "S". In some examples, as illustrated in FIG. 1, the magnetic token 104 is a free moving token with embedded permanent magnet. In some examples, the magnetic token 104 is a magnetized token and can be moved by a magnetic field. The magnetic token 104 can be moved due to the flow of the fluid. The magnetic token 104 can be moved by the magnetic field generated by the coil 106. The magnetic token 104 can be also moved by both the magnetic field and the fluid flow.

The coil 106 is configured to generate a first magnetic field to move the magnetic token 104 along a direction of the flow path of the fluid flow 101 and generate a second magnetic field to move the magnetic token 104 opposite to the direction of the flow path of the fluid flow 101. FIG. 4A shows a flow scenario 400 where the coil 106 generates a magnetic field 402 along the direction of the flow path of the fluid flow 101 in the conduit 102. The magnetic token 104 is moved by the magnetic field 402 in the conduit 102 along a direction 404 same as the flow path of the fluid flow 101. Thus, a forward velocity V1 of the magnetic token 104 can be a combination of a velocity V0 due to the magnetic field 402 and a velocity Vf of the fluid flow 101.

FIG. 4B shows another flow scenario 450 where the coil 106 generates a magnetic field 452 against (or opposite to) the direction of the flow path of the fluid flow 101, and the magnetic token 104 is moved by the magnetic field 452 in the conduit 102 in a direction 454 against the direction of the flow path of the fluid flow 101. That is, the direction 454 can be opposite to the direction of the flow path of the fluid flow 101. Thus, a backward velocity V2 of the magnetic token 104 can be the velocity V0 due to the magnetic field 452 minus the velocity Vf of the fluid flow 101.

The coil 106 can generate the magnetic fields 402 and 452 with the same intensity, for example, by using the same current with a reversed polarity. Thus, V0 can be the same. If there is no fluid flow, that is, Vf=0, then V1=V2. If there is any difference between V1 and V2, the difference between V1 and V2 can be related to the fluid flow Vf, for example, V1−V2 can be proportional to the fluid flow Vf.

When the magnetic token 104 is moving within the conduit 102 with the fluid flow 101 or the fluid flow 101 is bypassing the magnetic token 104 within the conduit 102, a friction can exist between the magnetic token 104 and the fluid flow 101 or between the fluid flow 101 and the conduit 102 or both, which can affect the moving velocity of the magnetic token 104. In some implementations, the conduit 102 is configured based on flow dynamics (for example, aerodynamics) to minimize (or even eliminate) the friction. For example, an inner diameter of a cross section of the conduit 102 can be determined based on an outer diameter or size of a cross section of the magnetic token 104. In some implementations, the magnetic token 104 is configured based on flow dynamics so that the friction on the magnetic token 104 can be minimized or even eliminated. For example, the outer diameter of the magnetic token 104 is determined based on the inner diameter of the conduit 102. In some implementations, both the conduit 102 and the magnetic token 104 are configured together based on flow dynamics to minimize or even eliminate the friction on the magnetic token 104.

As illustrated in FIG. 1, the conduit 102 can be a cylindrical tube extending along the longitudinal direction, and the magnetic token 104 can also extend along the longitudinal direction when put in the cylindrical tube. An inner diameter of the conduit 102 is larger than an outer diameter or size of the magnetic token 104. A surface profile of the magnetic token 104 can be also configured based on flow dynamics to minimize or eliminate the friction. For example, the surface profile can be curved.

In a particular example, the alternating magnetic field flow meter 100 is applied in a wellbore that includes upstream and downstream pipes to allow for a conservative full developed flow profile. The upstream and downstream pipes can be considered as conduits. The diameter of the magnetic token can be dependent on a pipe internal diameter (D) which in turn depends on a measured flow rate range (or capacity). The upstream straight pipe can have a length of 10*D, and the downstream straight pipe can have a length of 5*D.

Figure 5:
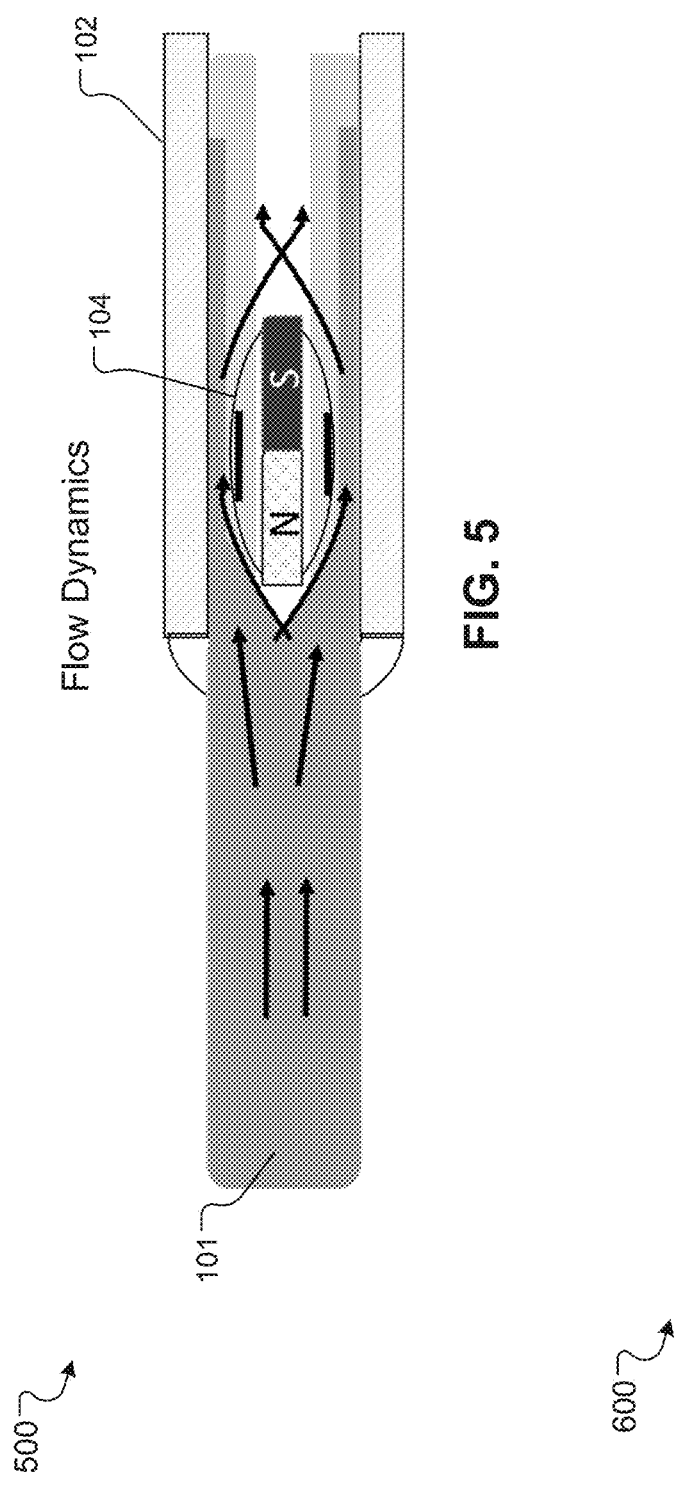
FIG. 5 shows flow dynamics of a fluid flow bypassing a magnetic token in a conduit.

FIG. 5 illustrates flow dynamics of the fluid flow 101 into the conduit 102. By configuring the conduit 102 and the magnetic token 104 based on flow dynamics and one or more properties of the fluid flow 101 (such as viscosity), the fluid flow 101 can form a thin jacket of fluid below and above the magnetic token 104 to minimize the friction between the fluid flow 101 and the magnetic token 104 and allow free movement of the magnetic token 104 or the fluid flow 101 or both.

As discussed before, the coil 106 can be configured to generate a first magnetic field to move the magnetic token 104 along the direction of the flow path and generate a second magnetic field to move the magnetic token 104 opposite to the direction of the flow path. The alternating magnetic field flow meter 100 can include a detector configured to detect a first electrical signal associated with the movement of the magnetic token 104 along the direction of the flow path, and a second electrical signal associated with the movement of the magnetic token 104 opposite to the direction of the flow path. The alternating magnetic field flow meter 100 can further include a processor configured to determine a flow rate of the fluid flow based on the detected first electrical signal and the detected second electrical signal.

In some implementations, as illustrated in FIG. 1, the piezoelectric sensor 110 can be used as the detector to detect the electrical signals associated with the movement of the magnetic token 104. The piezoelectric sensor 110 can use a piezoelectric effect to measure changes in mechanical force and convert the measured mechanical force changes to electrical charges. A voltage output of the piezoelectric sensor 110 can be directly proportional to the measured mechanical force changes. The piezoelectric sensor 110 can include a first surface 111 coupled to the inlet 103 of the conduit 102 and a second surface 113 coupled to the outlet 105 of the conduit 102. In some examples, the first surface 111 or the second surface 113 can be also positioned within the conduit 102, instead of on the inlet 103 or the outlet 105 shown in FIG. 1.

When the magnetic token 104 moves with a velocity to the inlet 103 or the outlet 105, the magnetic token 104 hits the first surface 111 or the second surface 113 with a mechanical force to deform the first surface 111 or the second surface 113. The piezoelectric sensor 110 is configured to detect a first voltage signal, for example, output voltage (b) in FIG. 1, when the magnetic token 104 is moved to deform the second surface 113 along the direction of the flow path and detect a second voltage signal, for example, output voltage (a) in FIG. 1, when the magnetic token 104 is moved to deform the first surface 111 opposite to the direction of the flow path. The flow rate of the fluid flow 102 can then be determined based on the first voltage signal and the second voltage signal. In some examples, the flow rate of the fluid flow is proportional to a voltage difference of the first voltage signal and the second voltage signal.

The coil 106 can be configured to alternately generate the first magnetic field and the second magnetic field for a number of times to move the magnetic token along the direction of the flow path of the fluid flow 101 and against the direction of the flow path of the fluid flow for the number of times. The piezoelectric sensor 110 can detect a plurality of first voltage signals and a plurality of corresponding second electrical signals when the magnetic token 104 is moved within the conduit 102 by the alternating first magnetic field and second magnetic field. Accordingly, the processor can determine the flow rate of the fluid flow 101 based on respective differences between the first electrical signals and corresponding second electrical signals.

Figure 6:
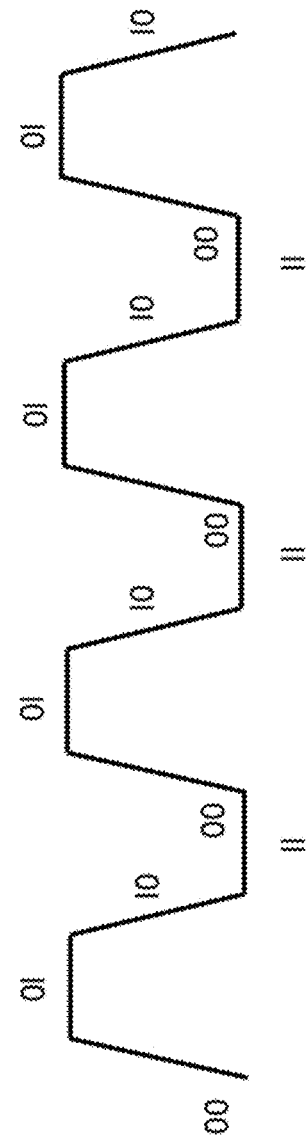
FIG. 6 shows an example operation pattern of an alternating magnetic field flow meter.

In a particular example, the alternating magnetic field flow meter 100 is configured to operate according to a pattern 600 shown in FIG. 6. Table 1 describes sequential phases with corresponding actions of the flow meter 100 during the phases.

TABLE 1

Actions at different phases

| Phase | Action |
|---|---|
| 00 | Energize magnetic field polarity with fluid flow |
| 01 | Measure forward velocity (V1), "with fluid flow" |
| 10 | Reverse magnetic field polarity |
| 11 | Measure backward velocity (V2) "opposite of fluid flow" |

Figure 7:
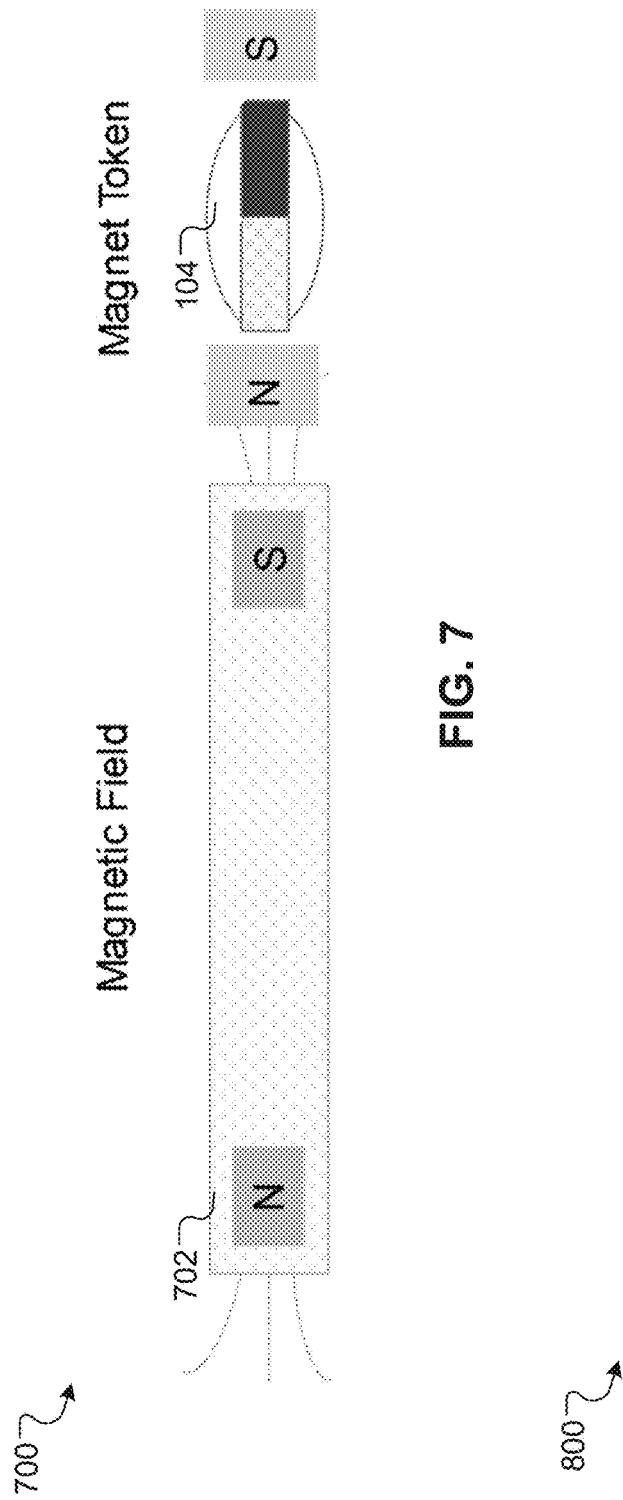
FIG. 7 shows an example of an alternating magnetic field flow meter at an initialization phase.

At an initialization phase, as illustrated in FIG. 7, the coil 106 is energized to generate a magnetic field 702 with a polarization opposite of the magnetic polarization of the magnetic token 104, forcing the magnetic token 104 to be initialized for a steady state position. At the initialization phase, there can be no fluid flow.

At phase 00 after the initialization phase, a current is used to energize the coil 106 to generate a magnetic field to force the magnetic token 104 to move within the conduit 102 along the direction of the flow path of the fluid flow 101, as illustrated in FIG. 4A. As discussed before, a forward flow velocity V1 of the magnetic token 104 can be a combination of a velocity V0 due to the magnetic field and a velocity Vf of the fluid flow 101.

When the magnetic token 104 moves at the flow velocity V1 to deform the second surface 113 of the piezoelectric sensor 110, for example, at the outlet 105 of the conduit 102, at phase 01, the piezoelectric sensor 110 outputs a voltage Vol1 for measuring the forward flow velocity V1 of the magnetic token 104.

After that, at phase 10, the current into the coil 106 is reversed to energize the coil 106 to generate a reversed magnetic field, which has a direction opposite to the direction of the flow path of the fluid flow 101. As illustrated in FIG. 4B, the magnetic token 104 is forced by the reversed magnetic field to move against the fluid flow 101. As discussed before, a backward flow velocity V2 of the magnetic token 104 can be the velocity V0 due to the reversed magnetic field minus the velocity Vf of the fluid flow 101.

When the magnetic token 104 moves at the flow velocity V2 to deform the first surface 111 of the piezoelectric sensor 110, for example, at the inlet 103 of the conduit 102, at phase 11, the piezoelectric sensor 110 outputs a second voltage Vol2 for measuring the backward flow velocity V2 of the magnetic token 104.

Thus, during a cycle including the four phases 00, 01, 10, 11, the piezoelectric sensor 110 outputs two voltages Vol1 and Vol2. A voltage difference between the two voltages Vol1 and Vol2 can be used to determine the flow rate Vf of the fluid flow 101.

As illustrated in FIG. 6, the alternating magnetic field flow meter 100 can operate for a number of cycles, and accordingly a number of voltage differences associated with the flow rate of the fluid flow 101 can be obtained. Each voltage difference can be used to determine a respective flow rate for the fluid flow 101. A final flow rate of the fluid flow 101 can be determined based on the determined respective flow rates. For example, the respective flow rates can be averaged to get an average result as the final flow rate. The alternating magnetic field flow meter 100 can operate according to the pattern in FIG. 6 at a sampling frequency, that is, a number of measurements per a unit of time. The higher the sampling frequency is, the more accurate the final flow rate can be determined.

Figure 8:
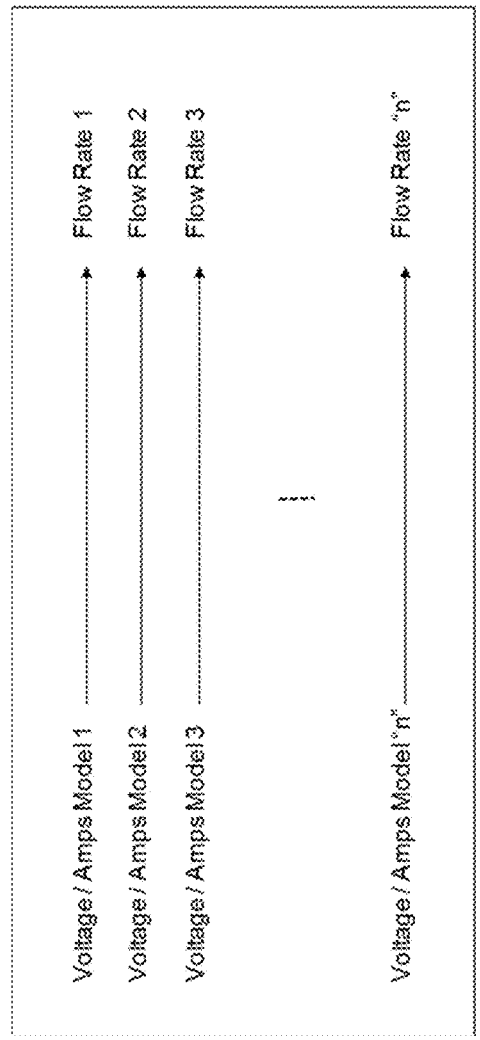
FIG. 8 shows an example model including associations between voltage/current differences and flow rates of fluid flows.

In some implementations, the alternating magnetic field flow meter 100 determines the flow rate of the fluid flow 101 based on the determined voltage difference and associations between voltage differences and respective flow rates for fluid flows. As illustrated in FIG. 8, the associations can be pre-determined based on a number of measurements of relationships between the voltage differences (or current differences) and the flow rates of the fluid flows. In some examples, variant measurements are used to create a representative model. The model can be analyzed and correlated against a predicted laboratory prepared scheme to determine the flow rate of the fluid. For example, fluid flows with known flow rates can be used, and corresponding voltage differences measured by the alternating magnetic field flow meter 100 can be obtained, as discussed before. The model can be based on the known flow rates and the measured corresponding voltage differences. Thus, the model can yield a predictive flow rate based on a corresponding voltage difference measured by the alternating magnetic field flow meter 100 when a fluid flow flows through the conduit 102 with an unknown flow rate. The model can be updated with the determined flow rate and the measured voltage difference.

Figure 9:
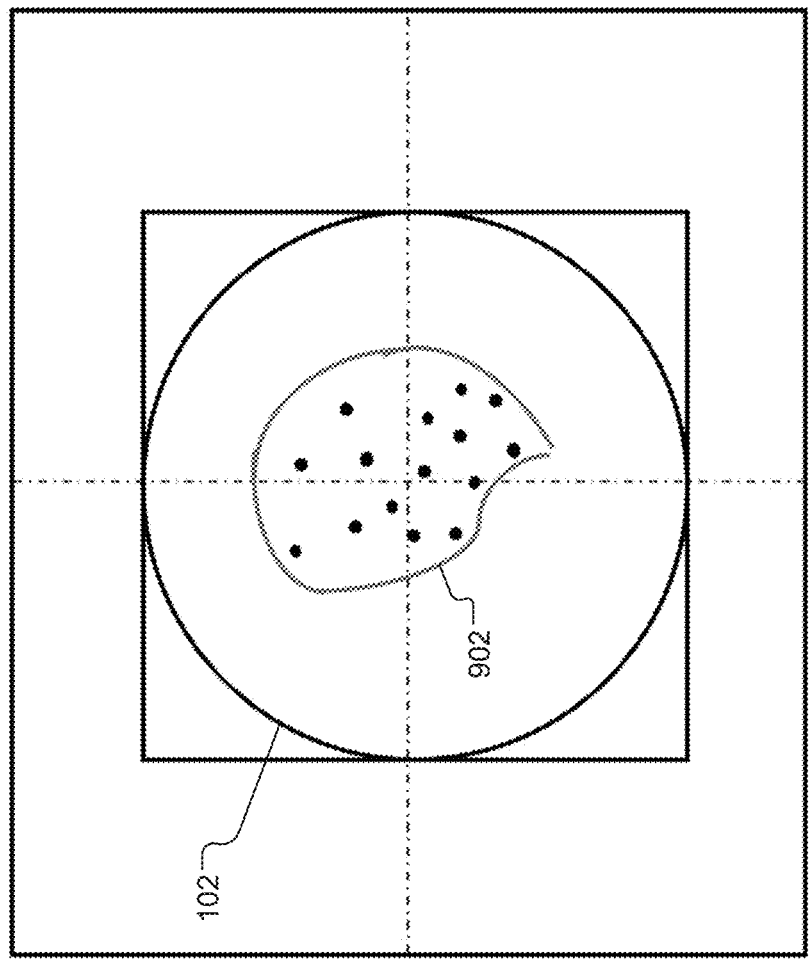
FIG. 9 shows an example sample contaminant distribution over time in a conduit.

As discussed before, the fluid flow 101 can include a liquid flow, a gas flow, or a slurry flow. The fluid can include one or more matters that can affect the measurement performance of the alternating magnetic field flow meter 100. For example, the fluid can include contaminants such as black powder, which can affect a measurement performance of the alternating magnetic field flow meter 100. FIG. 9 shows a schematic diagram 900 of an example sample contaminant distribution (or projection) 902 over time viewed from a cross section of the conduit 102. To improve the performance, the alternating magnetic field flow meter 100 can be calibrated, for example, by applying a correction factor on the determined flow rate for the fluid flow 101. The correction factor can be determined based on one or more properties of the fluid flow 101, for example, contaminants in the fluid flow 101, a flow volume, and a flow time.

Figure 10:
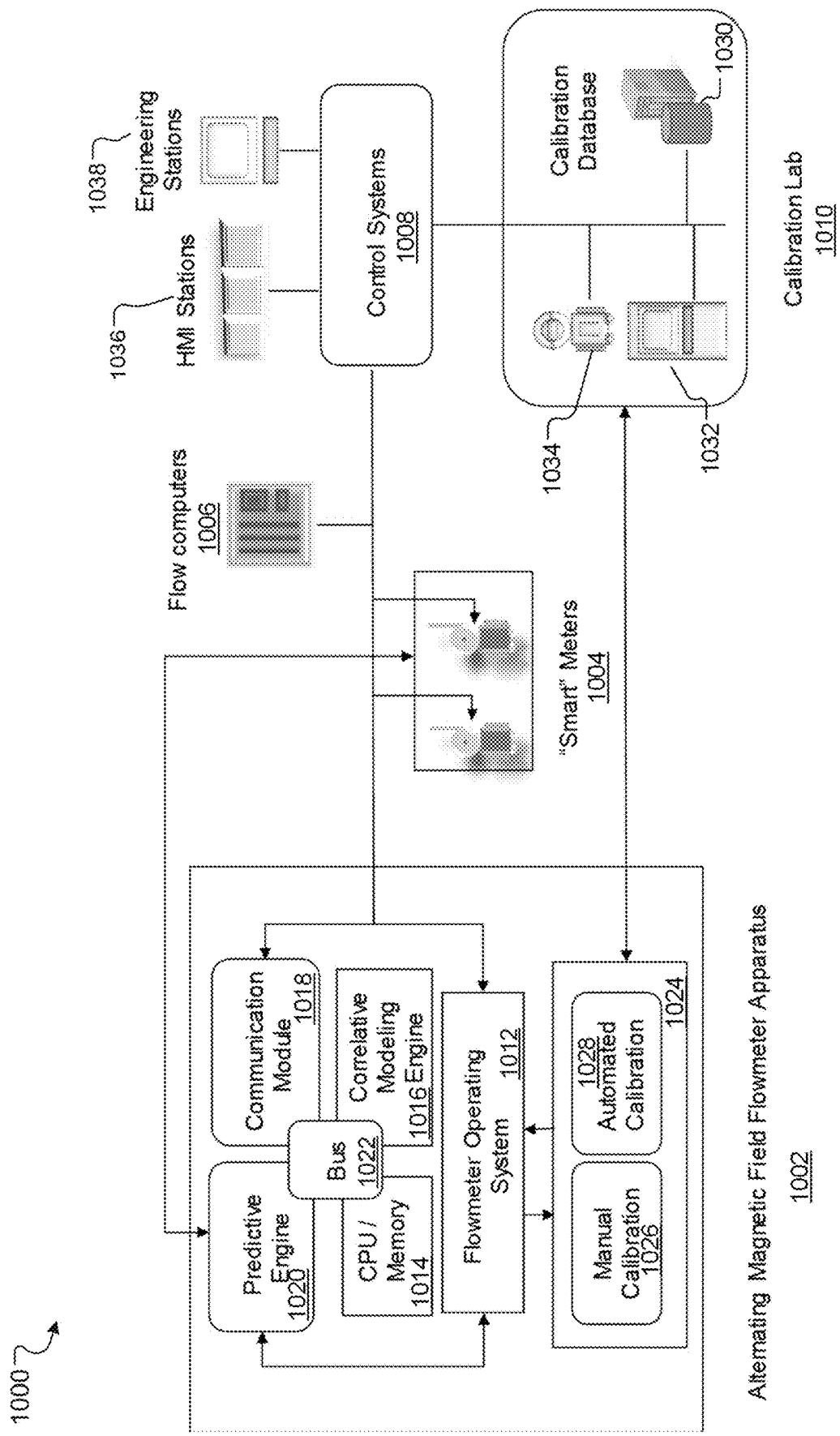
FIG. 10 is a schematic diagram of an example system including an alternating magnetic field flow meter with calibration capability.

The calibration process for the alternating magnetic field flow meter 100 can be performed using a manual process, an automated process, or both. FIG. 10 is a schematic diagram of an example system 1000 including an alternating magnetic field flow meter apparatus 1002 that can realize manual calibration and automated calibration. The flow meter apparatus 1002 can be the alternating magnetic field flow meter 100 of FIG. 1.

In some implementations, the system 1000 includes at least one of one or more smart meters 1004, one or more flow computers 1006, one or more control systems 1008, or a calibration lab 1010, which can communicate with each other via a network. The network can include a large computer network, such as a local area network (LAN), wide area network (WAN), the Internet, a cellular network, a satellite network, a mesh network, one or more wireless access points, or a combination thereof connecting any number of computing devices, mobile clients, fixed clients, and data servers.

Each of the smart meters 1004 is configured to exchange contaminant distribution patterns of past calibration experiences with other flow meters, servers or systems using the network. The flow meters in the system 1000, including the smart meters 1004 and the alternating magnetic field flow meter apparatus 1002, can include any suitable types of flow meters with any suitable principles of operation. The flow meters can be configured to perform periodic calibration to maintain their accuracies. The frequency and extent of calibration of a flow meter may vary depending on a type of the flow meter and an application of the flow meter.

The flow computers 1006 can include one or more processors configured to implement a computer logic to calibrate flow meters on regular intervals via the network. The calibration lab 1010 can include a calibration database 1030 for storing calibration information, one or more laboratory instruments 1032, and one or more flow meters 1034. The calibration lab 1010 can perform laboratory tests, for example, using the laboratory instruments 1032 and the flow meters 1034, with known contaminant distribution patterns. The calibration lab 1010 can also communicate with a number of flow meters and be configured to collect calibration information from the flow meters and transmit relevant calibration information to each of the flow meters. The control systems 1008 can control operations of flow meters via the network. For example, the control systems 1008 can perodicially feed calibration information to the flow meters. The control systems 1008 can be connected to one or more human machine interface (HMI) stations 1036 or one or more engineering stations 1038 or both.

In some implementations, the flow meter apparatus 1002 has a number of components including a flow meter operating system 1012, a CPU/memory 1014, a correlative modeling engine 1016, a communication module 1018, and a predictive engine 1020. The components can communicate with each other via a system bus 1022. The operating system 1012 can include Windows, Unix, Linux, or any suitable operating system. The CPU/memory 1014 can include one or more processors and one or more storage media. The communication module 1018 is configured to communicate with remote devices or systems, for example, the smart meters 1004, the flow computer 1006, or the control systems 1008, via the network. In some examples, the communication module 1018 includes one or more transceivers that can transmit wireless signals to the remote devices or systems. In some examples, the communication module 1018 includes a network interface circuit for wired communication with the remote devices or systems.

The correlative modeling engine 1016 is configured to provide a correlative model associating voltage (or current) differences and flow rates of fluid flows, for example, the model illustrated in FIG. 8. As discussed before, the correlative model can be used to yield a predictive flow rate based on a corresponding voltage difference measured by the alternating magnetic field flow meter apparatus 1002 for a fluid flow with an unknown flow rate, for example, by the correlative modeling engine 1016.

The flow meter apparatus 1002 can be an inferential meter. The correlative modeling engine 1016 can be configured to correlate a to-be-measured variable with the flow rate of the fluid flow using an associated phenomenon. For example, the correlation can be between the flow rate of the fluid flow and a mechanical speed of travel of suspended/energized rings, a travel time, current pulsations, or a combination thereof. In some cases, the correlation process is based on empirical testing rather than detailed mathematical computation. The alternating magnetic field flow meter apparatus 1002 can be initially tested at a lab, for example, the calibration lab 1010, to generate a performance curve to establish a relation between measured variables and resulting flow rates across the meter's operational range. The performance curve can be generated at different testing conditions covering a range of variables impacting the meter's performance such as temperature, density, pressure, viscosity, etc.

The predictive engine 1020 is implemented by a learning neural-network/fuzzy logic configured to predict a performance-affecting contaminant pattern in a fluid flow, for example, based on accumulated past (or previous) experiences or experimental results or both. The predicted pattern can be used to calculate a correction factor for a flow rate of the fluid flow. For example, the correction factor can be used to calibrate the predicted flow rate by the correlative modeling engine 1016. This can work for situations where contaminants are known to follow un-even distribution pattern over fixed volume in specific period of time interval. This also can work for situations where the system 1000 includes smart flowmeters 1004 that can share contaminant distribution patterns of past (or previous) experiences which can be digested by the neural network logic on the flow meter 1002 to predict an accuracy variance, and eventually calculate the correction factor. A meter accuracy variance can be calculated using parameters such as flow, contaminant distribution factor, and time. This variance is changing over time affecting the accuracy of a flow meter, and the computer logic can be also constantly calibrating the meter with this variance in % of a final meter reading. This logic can be implemented on the flow meter 1002 itself (for example, in the predictive engine 1020), or on the flow computers 1006 to be pushed on regular intervals via the network.

The flow meter apparatus 1002 can have a calibration component 1024 including a manual calibration module 1026 and an automated calibration module 1028. The manual calibration module 1026 is configured so that the flow meter apparatus 1002 can be manually calibrated on-line either directly against a bi-directional prover or indirectly against a master flow meter that has a higher accuracy. In some cases, the flow meter apparatus 1002 can be removed from service and sent for offline calibration, for example, in a proving station or a calibration lab such as the calibration lab 1010.

The automated calibration module 1028 can communicate with the calibration lab 1010 to get calibration information. The calibration information can include laboratory testing results for known contaminants distribution patterns or calibration information from other flow meters under a same working environment or both. The automated calibration module 1028 can communicate the calibration information to the flow meter operating system 1012 and to the predictive engine 1020 to determine a correction factor based on the calibration information.

In some cases, a fluid to be measured has a consistent composition or even contaminant distribution or both. In some implementations, an initial calibration is performed on the flow meter apparatus 1002, where the fluid to be measured can flow through the flow meter apparatus 1002 at various flow rates, for example, representing 0%, 25%, 50%, 75%, and 100% of a desired flow rate range. In some implementations, the calibration is done using a lab-based calibration table, a theoretical calibration, a software simulation (for example, computational fluid dynamics (CFD) modeling), or any combination thereof. In some implementations, a calibration process for the flow meter apparatus 1002 is performed using an automated process. A correction factor can be applied based on calibration information from laboratory experiences that have been tested and recorded in laboratory (for example, in the calibration lab 1010) for contaminants known to follow even distribution patterns over a fixed volume in a specific period of time interval. The calibration information can be fed into a newly deployed flow meter, for example, the flow meter apparatus 1002, by performing a system update through the control systems 1008 via the network, or from a local service data port of the flow meter. The calibration information can be housed in the calibration database 1030. The calibration database 1030 is configured to provide calibration information to a number of participating flow meters through periodically-sent feeds from the control systems 1008 via the network. The feeds can contain calibration information (for example, % of accuracy degradation per unit of time) archived (in the database 1030) for flow meters under the same working environment.

In some cases, a fluid to be measured has inconsistent composition or uneven contaminant distribution or both. The flow meter apparatus 1002 can be configured to be an intelligent remote calibration system.

In some implementations, calibration curves are loaded and stored in the meter electronics. Calibration tables (or recipes) for different known fluid compositions can be developed based on lab or field testing. Then the calibration tables (or recipes) can be fed to or programmed into the meter electronics, for example, through a hand-held communicator or directly from the control system 1008. The calibration table (or recipes) can be selected based on the fluid to be measured (or the passing fluid) at a particular time of operation.

In some implementations, as discussed before, the flow meter apparatus 1002 can be an inferential meter configured to use inferential modeling, for example, by the correlative modeling engine 1016. A calibration table can be developed based on the most common operating mode or condition (or a base case). This model can be then continuously updated through simple measurement of a number of process variables such as pressure, temperature, or optical footprint. The inferential modelling can include real-time estimations of un-measured properties through offline development and online deployment of empirical models and data-driven process performance monitoring. The inferential modeling can be used to provide real-time estimations of product qualities otherwise available only through infrequent online or laboratory analysis.

In some implementations, as discussed before, the flow meter apparatus 1002 can be configured to use at least one of a fuzzy logic or a neural network logic, for example, by the predictive engine 1020. The basic calibration model can be continuously updated by implementing the neural network logic that predicts performance-affecting parameters based on accumulated data from past experiences of the flow meter apparatus 1002 or other meters or both.

In some implementations, multiple flow meters, including the smart meters 1004 and the alternating magnetic field flow meter apparatus 1002, are installed or deployed in the system 1000, the functionality of inter-meter communications can be added to the flow meters. The inter-meter communications can be either through peer-to-peer communications or communications through the control system 1008 or the network. The inter-meter communications can be used to enhance calibration tables, verify meter status, detect change in pattern, and/or conduct mass balance.

A flow meter, for example, the alternating magnetic field flow meter apparatus 1002, in the multiple-meter installations (or in the system 1000) can be designed and configured to communicate with other flow meters within the same system 1000 and also with meters in other systems through standard industry interfaces. The flow meter can be connected to the other flow meters or the other systems through point-to-point connection, physical layer bus, remote input/output (I/O) module or wirelessly. For example, direct communication can be enabled between the flow meters in the system 1000 (for example, through the physical layer) if the flow meters are part of a digital network such as Foundation Fieldbus or process fieldbus (profibus). Data exchange between the flow meters can be used to update calibration tables through a validated model, or data can be used as inputs to calculate material mass balance. If there is a relationship between readings of two meters (such as, ratio), data can be used to enhance ration control. As discussed below, a voting system among the flow meters can make the readings more reliable. Data exchange between the flow meters can extend beyond the system 1000. As a system can be interfaced with another system through standard interfaces, such as HTTP, FTP, OPC, or serial link (e.g., RS 425), data transfer across the systems can be used to enhance measurement data quality and other purposes as mentioned before.

In some implementations, a voting system can be built among flow meters to implement automatic calibration. For example, the automatic calibration module 1028 of the flow meter apparatus 1002 can include an on-board voting module configured to build the voting system with other flow meters.

Figure 11A:
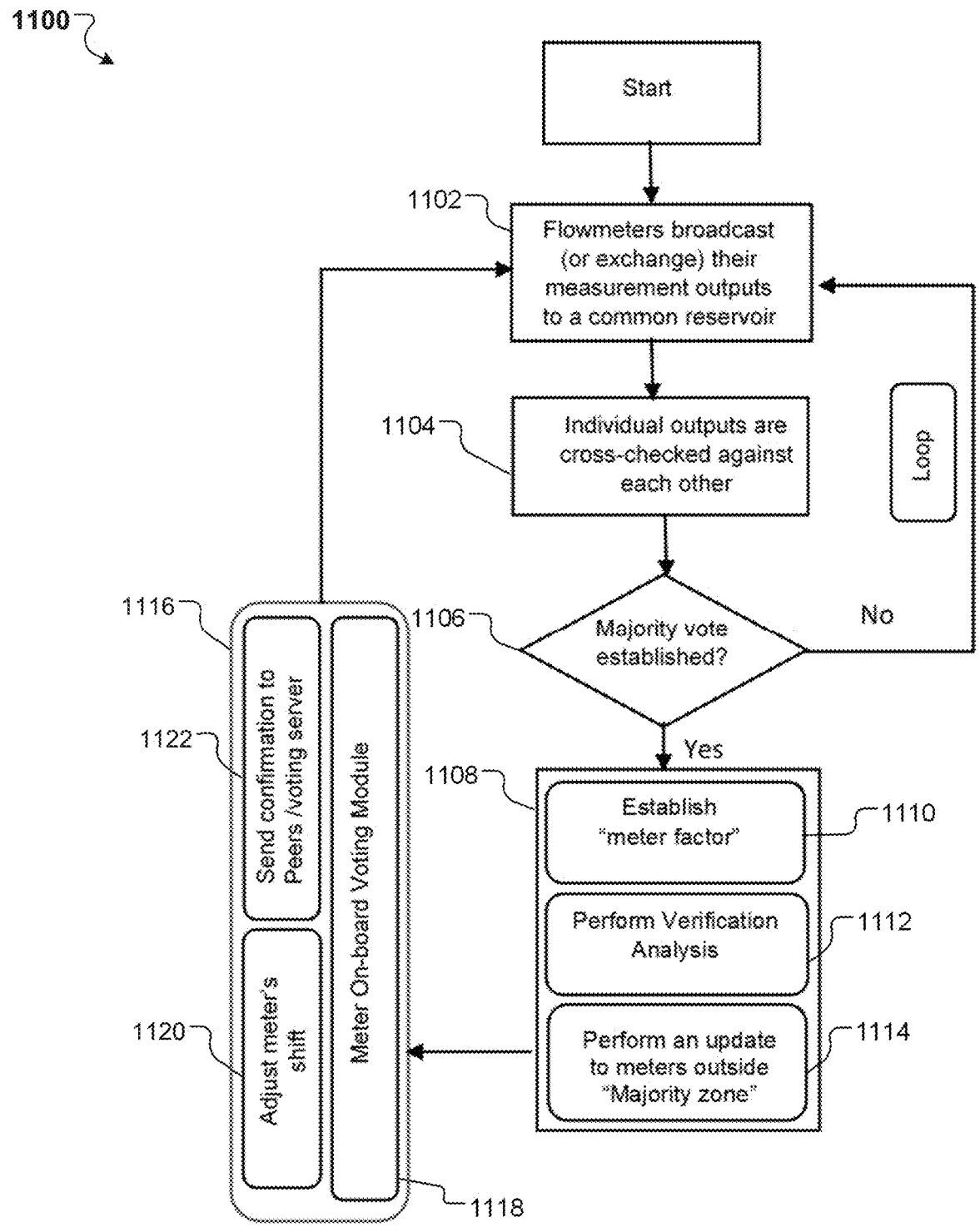
FIG. 11A is a flowchart of an example process of a voting logic for flow meters in a similar condition environment according to the present disclosure.
Figure 11B:
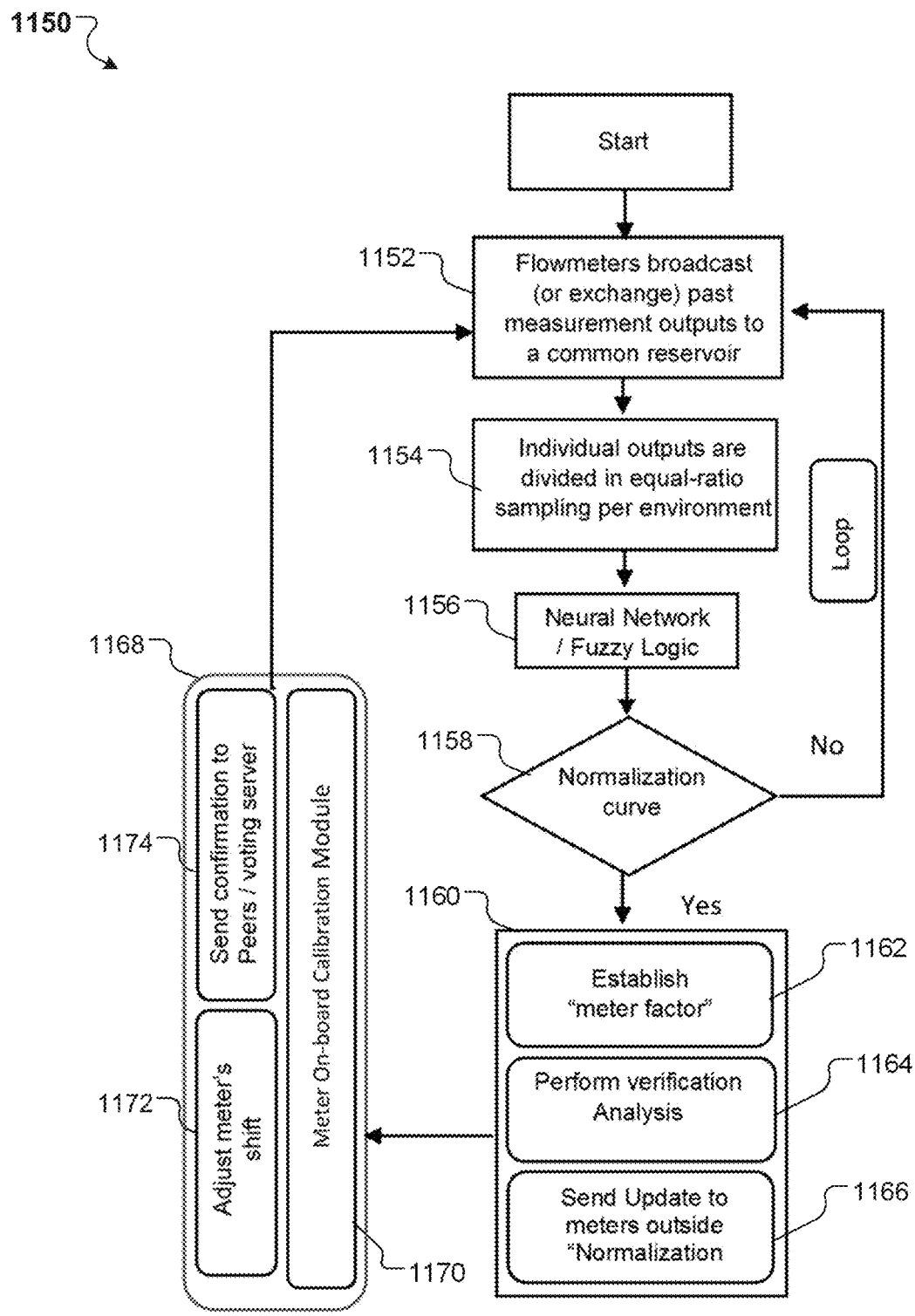
FIG. 11B is a flowchart of an example process of a voting logic for flow meters in a diverse condition environment according to the present disclosure.

FIG. 11A shows an example process 1100 of a voting logic for flow meters in a similar condition environment. FIG. 11B shows an example process 1150 of a voting logic for flow meters in a diverse condition environment. The flow meters can include the alternating magnetic field flow meter apparatus 1002, the smart meters 1004, other flow meters in the system 1000, and/or flow meters in other systems in communication with the system 1000. The process 1100 can be performed by a control system in communication with the flow meters, for example, the control system 1008 of FIG. 10. The process 1150 can be also performed by the control system. The control system can include one or more processors and one or more storage media. The control system can include a voting server in communication with on-board voting modules of the flow meters.

Referring to FIG. 11A, the flow meters broadcast (or exchange) their measurement outputs to a communication reservoir (1102). The communication reservoir can be included in the control system. Individual measurement outputs are cross-checked against each other (1104), for example, by the processors in the control system. Then, it is determined whether a majority vote is established (1106), for example, by the processors in the control system. If the majority vote is determined not to be established, the process 1100 goes back to step 1102, which forms a loop. If the majority vote is determined to be established, the process 1100 goes to step 1108. Meters associated with the majority vote form a majority zone. During step 1108, a meter factor can be established (1110). The meter factor is used to adjust measurement outputs of meters outside the majority zone back to the majority vote. Verification analysis is performed (1112), for example, to verify whether the measurement outputs of meters outside the majority zone adjusted with the meter factor can be within the majority vote. An update can be performed to the meters outside the majority zone (1114), for example, the established meter factor can be transmitted to the meters outside the majority zone.

Each of the meters outside the majority zone performs step 1116, which can include receiving the meter factor or other information by a meter on-board voting module (1118) and automatically adjusting the meter's shift to bring itself back to the majority zone using the received meter factor (1120). That is, the meter can automatically calibration itself based on the received meter factor. Once the meter's measurement output is brought back to the majority zone, the meter sends a confirmation signal to peers (e.g., other flow meters)/the voting server on the control system (1122). Then the process 1100 goes back to step 1102. This process 1100 can be ongoing and continually relying on smart electronics to keep establishing the votes and adjusting the meters' shifts.

Referring to FIG. 11B, the example process 1150 shows a voting logic for flow meters in a diverse condition environment. The flow meters broadcast (or exchange) their measurement outputs to a communication reservoir (1152). The communication reservoir can be included in the control system. Individual measurement outputs are divided in equal-ratio sampling per environment (1154). Based on the corresponding condition environments of sample fluids measured in the flow meters, the individual measurement outputs of the flow meters can be divided into a number of groups. Each group can include measurement outputs of respective flow meters in a similar sampling condition environment.

Each group of measurement outputs is analyzed by a neural network/fuzzy logic in the control system (1156). The neural network/fuzzy logic can be similar to the neural network/fuzzy logic in the predictive engine 1020. The neural network/fuzzy logic determines whether the measurement outputs in the group can be fit with a normalization curve (1158). The normalization curve can have a normal distribution or Gaussian distribution. If the measurement outputs in the group are determined not to be fit with a normalization curve, the process 1150 goes back to step 1152, which forms a loop. If the measurement outputs in the group are determined to be fit with a normalization curve, the process 1150 goes to step 1160. Meters with measurement outputs on the normalization curve can be noted as meters inside the normalization. Meters with measurement outputs off the normalization curve can be noted as meters outside the normalization. During step 1160, a meter factor can be established (1162). The meter factor is used to adjust measurement outputs off the normalization curve to be on the normalization curve. Verification analysis is performed (1164), for example, to verify whether the measurement outputs off the normalization can be adjusted by the meter factor to be on the normalization curve. An update can be performed to the meters outside the normalization (1166), for example, the established meter factor can be transmitted to the meters outside the normalization.

Each of the meters outside the normalization performs step 1168, which can include receiving the meter factor or other information by a meter on-board voting module (1170) and automatically adjusting the meter's shift to bring itself back to the normalization curve using the received meter factor (1172). That is, the meter can automatically calibration itself based on the received meter factor. Once the meter's measurement output is brought back to the normalization curve, the meter sends a confirmation signal to peers (e.g., other flow meters)/the voting server on the control system (1174). Then the process 1150 goes back to step 1152. This process 1150 can be ongoing and continually relying on smart electronics to keep analyzing normalization within the measurement outputs of the meters and adjusting the meters' shifts.

Figure 2:
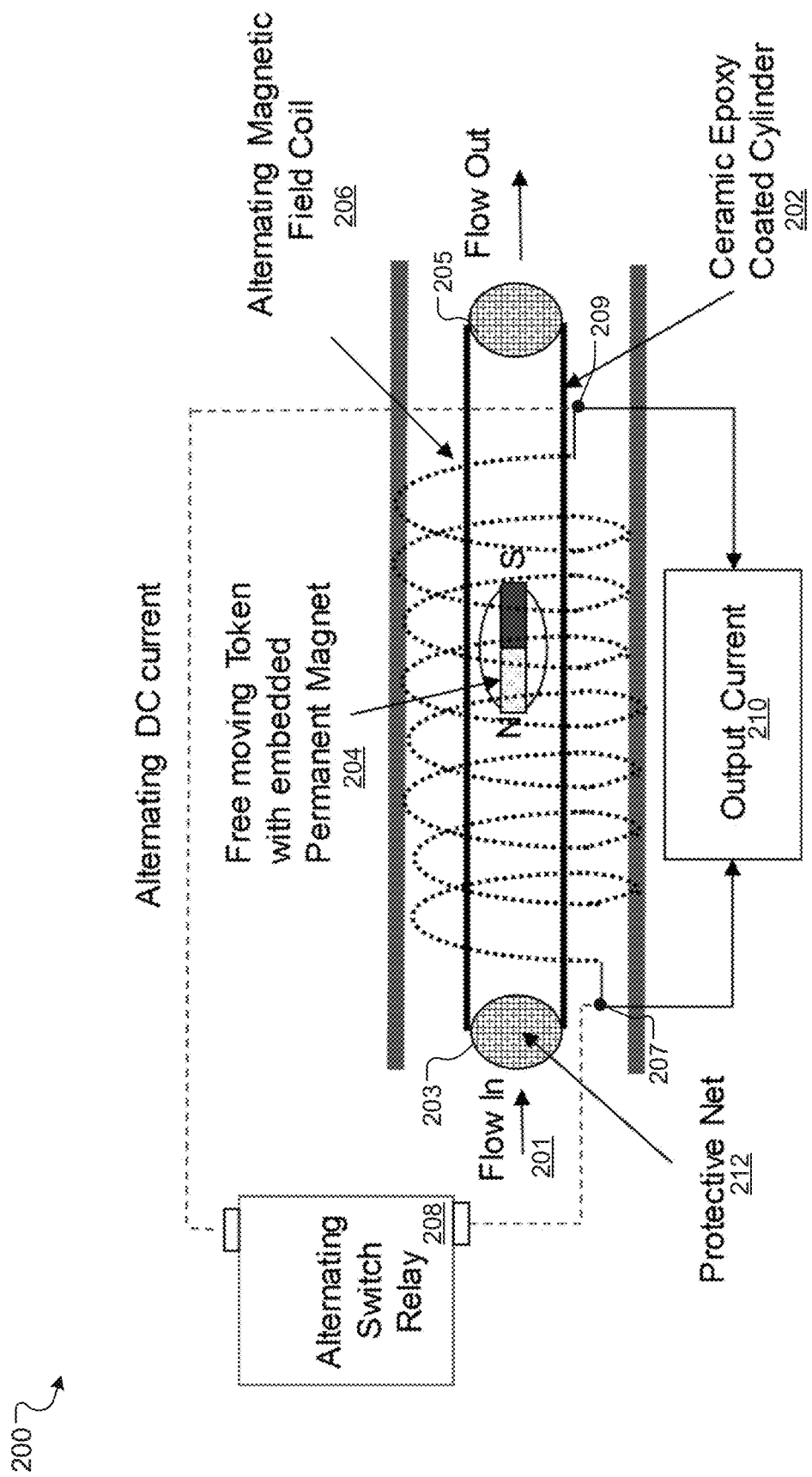
FIG. 2 is a schematic diagram of another example alternating magnetic field flow meter using an electromagnetic coil for detection according to the present disclosure.

FIG. 2 is a schematic diagram of another example alternating magnetic field flow meter 200 using an electromagnetic coil for detection according to the present disclosure. Compared to the alternating magnetic field flow meter 100 of FIG. 1, the alternating magnetic field flow meter 200 does not use the piezoelectric sensor 110 or any other sensor for detection. Instead, the alternating magnetic field flow meter 200 uses the electromagnetic coil configured to generate a magnetic field.

In some implementations, the alternating magnetic field flow meter 200 includes a conduit 202, a magnetic token 204, and an electromagnetic coil 206. The conduit 202, the magnetic token 204, and the coil 206 can be similar to the conduit 102, the magnetic token 104, and the coil 106 of FIG. 1, respectively. A fluid flow 201, for example, the fluid flow 101 of FIG. 1, flows into the conduit 202 through an inlet 203 and out from an outlet 205. The conduit 202 guides the fluid flow 201 along a flow path. Protective nets 212 can be applied on the inlet 203 and the outlet 205 to keep the magnetic token 204 moving within the conduit 202.

The coil 206 can be a coiled wire including electrical nodes 207 and 209. The coil 206 is used as a magnetic field generator and configured to receive alternating DC currents from a power source 208 including an alternating switch relay through the nodes 207 and 209. The coil 206 can generate alternating magnetic fields based on the alternating DC currents to move the magnetic token 204 back and forth within the conduit 202.

The alternating magnetic field flow meter 200 includes a current detector 210 with a first electrode coupled to the electrical node 207 of the coil 206 and a second electrode coupled to the electrical node 209. The current detector 210 is configured to receive a current output from the coil 206 generated via electromagnetic induction by a time-varying magnetic field caused by the movement of the magnetic token 204.

In some implementations, the coil 206 is configured to generate a first magnetic field to move the magnetic token 204 along a direction of the flow path of the fluid flow 201 for a first period of time and then de-energize the first magnetic field, such that the current detector 210 receives a first current signal in response to the magnetic token 204 moving in the electromagnetic coil 206 without the first magnetic field and along the direction of flow path. The coil 206 is also configured to generate a second magnetic field to move the magnetic token 204 opposite to the direction of the flow path for a second period of time and then de-energize the second magnetic field, such that the current detector 210 receives a second current signal in response to the magnetic token 204 moving in the electromagnetic coil 206 without the second magnetic field and opposite to the direction of flow path. A flow rate of the fluid flow 201 can be determined based on the first current signal and the second current signal detected by the current detector 210. For example, the flow rate can be proportional to a current difference of the first current signal and the second current signal.

Similar to the alternating magnetic field flow meter 100 of FIG. 1, the alternating magnetic field flow meter 200 can operate in a cycle including a series of steps.

First step: the coil 206 is initially energized to generate a first magnetic field have a direction same as the direction of the flow path of the fluid flow 201, and the magnetic token 204 moves horizontally along the conduit 202 with a flow velocity V1.

Second step: as the magnetic token 204 starts to move horizontally along the conduit 202 with a flow velocity V1, the first magnetic field is momentarily de-energized to generate a first current indicative of the flow velocity V1, and the first current is detected by the current detector 210.

Third step: the coil 206 is re-energized by reversing the polarity of the input current to generate a second magnetic field with a direction opposite to the direction of the flow path of the fluid flow 201, driving the magnetic token 204 in the opposite of the flow path direction by the force or flux of the second magnetic field with a flow velocity V2.

Fourth step: as the magnet starts to move horizontally along the conduit 202 with a flow velocity V2, the second magnetic field is momentarily de-energized to generate a second current indicative of the flow velocity V2, and the second current is detected by the current detector 210.

The flow rate Vf of the fluid flow 201 in the conduit 202 can be determined based on the detected first current and second current. In a particular example, the flow rate Vf is proportional to a difference of the flow velocities V1 and V2, and is accordingly proportional to a difference of the first current and the second current. A volumetric flow rate Q=V*A (cross-sectional area), and/or a mass flow rate M=Q*Density can be determined accordingly.

Similar to the alternating magnetic field flow meter 100 of FIG. 1, the alternating magnetic field flow meter 200 can operate for a number of cycles at a sampling frequency, as illustrated in FIG. 6. The alternating magnetic field flow meter 200 can also determine the flow rate of the fluid flow using a correlative model, as illustrated in FIG. 8. The alternating magnetic field flow meter 200 can be similar to the flow meter apparatus 1002 of FIG. 10 and achieve manual calibration or automatic calibration or both on the flow rate of the fluid flow 201.

Figure 12:
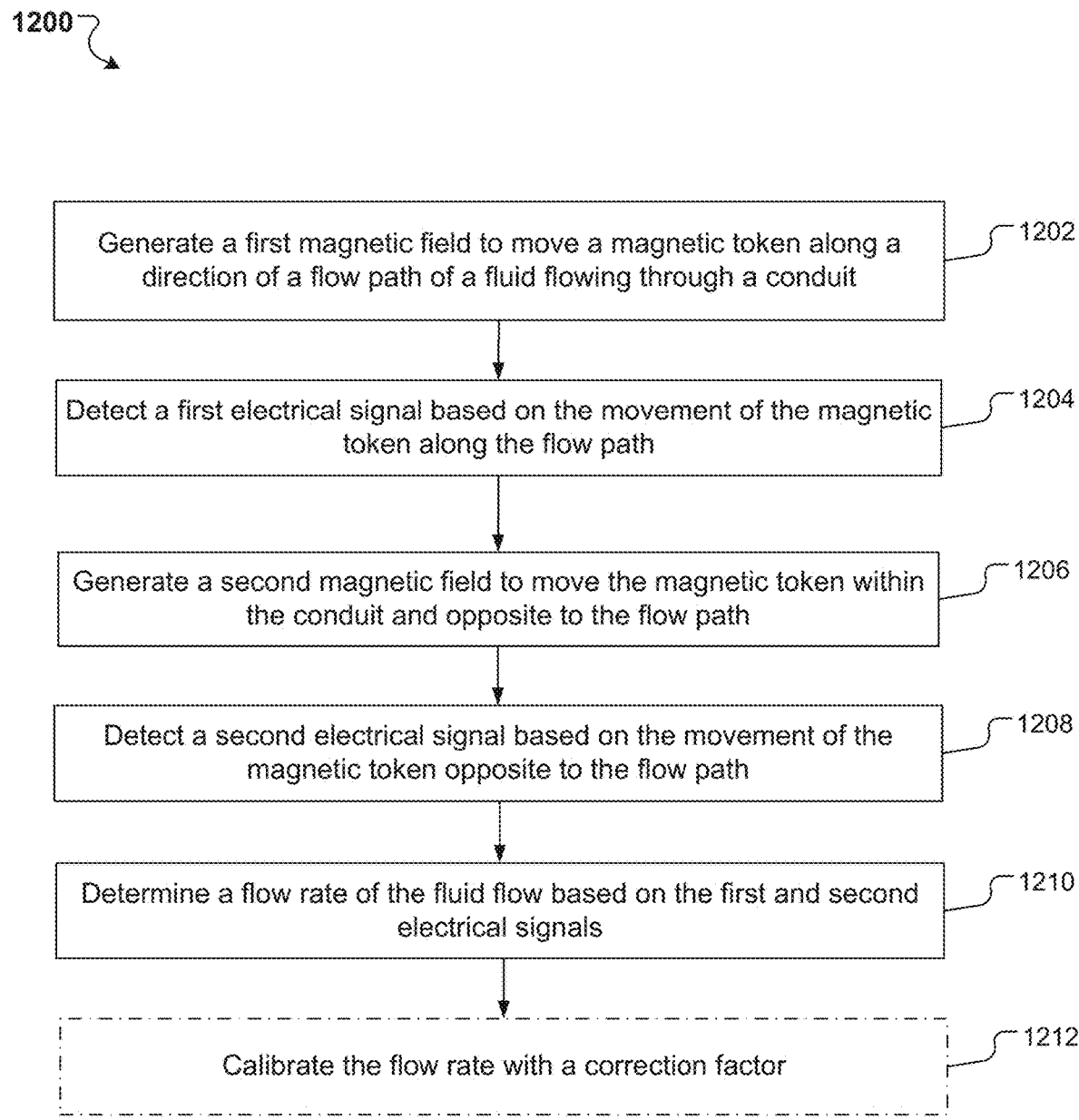
FIG. 12 is a flowchart of an example process of measuring a flow rate of a fluid flow using an alternating magnetic field flow meter according to the present disclosure.

FIG. 12 is a flowchart of an example process 1200 of measuring a flow rate of a fluid flow using an alternating magnetic field flow meter according to the present disclosure. The alternating magnetic field flow meter can be the alternating magnetic field flow meter 100 of FIG. 1, the alternating magnetic field flow meter 200 of FIG. 2, or the flow meter apparatus 1002 of FIG. 10.

The fluid can include liquid, gas, slurry, or any combination thereof. The fluid can include a conductive material, a non-conductive material, or any combination thereof. The fluid flows through a conduit of the flow meter and configured to guide the fluid along a flow path. A free moving magnetic token, for example, the magnetic token 104 of FIG. 1, is arranged within the conduit and movable along the conduit.

A first magnetic field is generated to move the magnetic token along a direction of the flow path of the fluid flow (1202). The alternating magnetic field flow meter can include an electromagnetic coil, for example, the coil 106 of FIG. 1, configured to generate the first magnetic field based on an input current.

A first electrical signal is detected based on the movement of the magnetic token along the flow path (1204). In some implementations, the flow meter includes a piezoelectric sensor, for example, the piezoelectric sensor 110 of FIG. 1.

The first electrical signal can be detected by detecting a first voltage signal when the magnetic token is moved to deform a first surface of the piezoelectric sensor coupled to an outlet of the conduit. In some implementations, the flow meter uses the electromagnetic coil itself to detect the movement of the magnetic token. After the coil generates the first magnetic field for a first period of time, the first magnetic field is de-energized by stopping to provide a current to the coil, such that the magnetic token moves in the coil without the first magnetic field and along the direction of flow path to generate a first current signal. The flow meter can include a current detector, for example, the current detector 210 of FIG. 2, to detect the first current signal.

A second magnetic field is generated to move the magnetic token within the conduit and opposite to the direction of the flow path of the fluid flow (1206). As discussed before, the second magnetic field can be generated by reversing a polarity of the current into the electromagnetic coil.

A second electrical signal is detected based on the movement of the magnetic token opposite to the direction of the flow path (1208). In some implementations, the second electrical signal is detected by detecting a second voltage signal when the magnetic token is moved to deform a second surface of the piezoelectric sensor coupled to an inlet of the conduit. In some implementations, after the coil generates the second magnetic field for a second period of time, the second magnetic field is de-energized by stopping to provide the reversed current to the electromagnetic coil, such that the magnetic token moves in the electromagnetic coil without the second magnetic field and opposite to the direction of flow path to generate a second current signal. The second current signal can be detected by the current detector.

A flow rate of the fluid flow is determined based on the first and second electrical signals (1210). In some implementations, the flow rate is determined based on the first and second voltage signals detected by the piezoelectric sensor. In some implementations, the flow rate is determined based on the first and second current signals detected by the current detector.

In some examples, the flow rate is determined based on a difference between the first electrical signal and the second electrical signal and a correlative model including associations between differences of electrical signals and respective flow rates. The correlative model can be determined based on known flow rates, for example, the model in FIG. 8.

In some examples, the flow meter repeats steps 1202, 1204, 1206 and 1208, for a number of times. That is, the flow meter alternately generates the first magnetic field and the second magnetic field, detects a plurality of first electrical signals and a plurality of corresponding second electrical signals, and determines the flow rate of the fluid flow based on respective differences between the first electrical signals and corresponding second electrical signals.

Optionally, the flow rate can be calibrated with a correction factor (1212). In some examples, when contaminants in the fluid flow follow an even distribution pattern, for example, determined by measurement, the correction factor is determined based on calibration information including contaminants known with even distribution patterns and corresponding correction factors. The flow meter can receive the calibration information from a calibration lab, for example, the calibration lab 1010 of FIG. 10. In some examples, when contaminants in the fluid flow follow an uneven distribution pattern, the flow meter can use a neural network logic to predict the contaminant distribution pattern for the fluid flow and generate the correction factor based on the predicted contaminant distribution pattern and accumulated calibration information including contaminant distribution patterns and associated accuracy variances of flow meters.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, such as, one or more modules of computer program instructions encoded on a tangible, non-transitory computer-storage medium for execution by, or to control the operation of, data processing apparatus. Alternatively or in addition, the program instructions can be encoded on an artificially generated propagated signal, such as, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus and special purpose logic circuitry may be hardware-based and software-based. The apparatus can optionally include code that creates an execution environment for computer programs, for example, code that constitutes processor firmware, a protocol stack, a database management system, an operating system, or a combination of one or more of them. The present specification contemplates the use of data processing apparatuses with or without conventional operating systems.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD-R, DVD-RAM, and DVD-ROM disks. The memory may store various objects or data, including caches, classes, frameworks, applications, backup data, jobs, web pages, web page templates, database tables, repositories storing business and dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include multiple user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), worldwide interoperability for microwave access (WIMAX), a wireless local area network (WLAN) using, for example, 902.11 a/b/g/n and 902.20, all or a portion of the Internet, and any other communication system or systems at one or more locations. The network may communicate with, for example, internet protocol (IP) packets, frame relay frames, asynchronous transfer mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and software, may interface with each other or the interface using an application programming interface (API) or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in any suitable language providing data in any suitable format. The API and service layer may be an integral or a stand-alone component in relation to other components of the computing system. Moreover, any or all parts of the service layer may be implemented as child or sub-modules of another software module, enterprise application, or hardware module without departing from the scope of this specification.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing may be advantageous and performed as deemed appropriate.

Moreover, the separation or integration of various system modules and components in the implementations described earlier should not be understood as requiring such separation or integration in all implementations, and it should be understood that the described program components and systems can generally be integrated together in a single software product or packaged into multiple software products.

Accordingly, the earlier provided description of example implementations does not define or constrain this specification. Other changes, substitutions, and alterations are also possible without departing from the spirit and scope of this specification. For example, instead of using an electromagnetic coil to generate an alternating magnetic field with an alternating current, one or more permanent magnets can be also configured to provide an alternating magnetic field for use in alternating magnetic field flow meters disclosed herein.

Generally, a Supervisory Control and Data Acquisition System (SCADA) includes automation software written to perform data acquisition requirements for an individual plant. The software controls command and data transfer between master stations (for example, server or servers and software responsible for communicating with the field equipment), Human Machine Interface (HMI) workstations in the control room, and field devices that are connected to Remote Terminal Units (RTU), for example, pressure transmitters, flow meters, and temperature sensors.

Unlike Distributed Control Systems (DCS), which are designed to carry out "regulatory" control algorithms (for controlled processes such as keeping the process within a "setpoint") within a specific area of the plant (risk area), supervisory control carries out "event-based" monitoring algorithms (for example, data-gathering) over a large geographical area. SCADA is a telemetry based process control command initiated from a Master Central Station (MCS). The initiation command can be sent either manually by an operator or automatically by an application to initiate an action or change the analog set point in a remotely located control station or RTU, or both. The command can be sent over a bidirectional (for example, in both directions) communications link using specific communication protocols. Such commands depend on having quality process-related event data and timely bidirectional confirmation and acknowledgment executing sequences between the master and the station, known as check before operate (CBO).

Master Stations can include multiple server instances (using virtualization services), distributed software applications, to enable SCADA network management including disaster recovery sites. A Master Station includes all communications and networking instrumentations required to communicate with RTUs and remote sites using bidirectional information transfer between master and remote terminals (of a communication channel). As part of SCADA operation, commands are sent by operators or by applications in binary or analog (setpoint) from the HMI station to field instruments connected to a particular RTU to provide a status reading or perform a certain remote action. The command originating from the HMI station must be delivered to its target as quickly as possible, typically in the order of seconds or sub-seconds. If a command cannot be delivered or acted upon, the SCADA system reports such to the operator.

Master Stations, HMIs, and RTUs use a communication medium that facilitates the signaling between these terminals, for example, a path between master station and an HMI, RTU, or a subsystem. This is part of an overall communications subsystem that performs the transmitting and receiving of digital information for the entire SCADA and uses media such as fiber optics, copper cabling, wireless and VSAT communications. RTUs are microprocessor-controlled electronic equipment that interfaces field instrumentations such as sensors, transmitters, and actuators to a DCS or SCADA by transmitting telemetry data to a master system.

In some implementations, the RTU can be connected to flow measurement instruments that measure fluids flow from wellheads, through distribution pipelines, or exiting from storage tanks. Flowmeter technologies are based on several working principles using mechanical and non-mechanical methods and modes of operations. For example, an electromagnetic flow meter can be used to measure a flow of an electrically conductive fluid along a flow path in a conduit. The electromagnetic flow meter makes use of electrodynamic induction and is operative to apply a magnetic field across the flow path. Charge carriers in the conductive fluid moved perpendicularly to the magnetic field causes the induction of a voltage across the conductive fluid. As the conductive fluid conducts electricity, the induced voltage can be measured by electrodes arranged approximately perpendicular to the flow direction of the fluid and the magnetic field, such as on both ends of the conduit. The voltage induced in the electrodes is proportional to the velocity of the fluid flow averaged over a cross section of the conduit, and accordingly proportional to the volume flow rate or massive flow rate of the fluid flow. However, such electromagnetic flow meters cannot measure non-conductive fluids. The present specification describes methods, apparatus, and systems for providing fluid flow measurements that can be used for both conductive fluids and non-conductive fluids with embedded fluid quality assessment, control, and management. This is achieved by utilizing a velocity variance of a free moving magnet in an alternating magnetic field coupled with a Total Dissolved Solids (TDS) measurement instrumentation controlled by a synchronizing procedure. Additionally, the meter community can use the interlinking network to communicate TDS readings as part of the previously disclosed auto-calibration method to provide a whole system TDS quality control and management.

The total dissolved solids (TDS) level is measured as a form of salinity metering. High TDS levels generally indicate hard water which causes scale buildup in pipes, valves, and filters, reducing performance and adding to boiler system maintenance and efficiency costs over the long term. In some fluids such as water, TDS is directly related to the conductivity of dissolved ionized solids in the fluids. Ions from the dissolved solids enable water to conduct an electrical current, which can then be measured to determine its salinity index. Since the alternating magnetic field flowmeters use current variance measurements to determine flow rate, the device can further be adapted with an electric charge emitter (EC) and a synchronizing clock to allow for an additional fluid quality measurement function.

Figure 13:
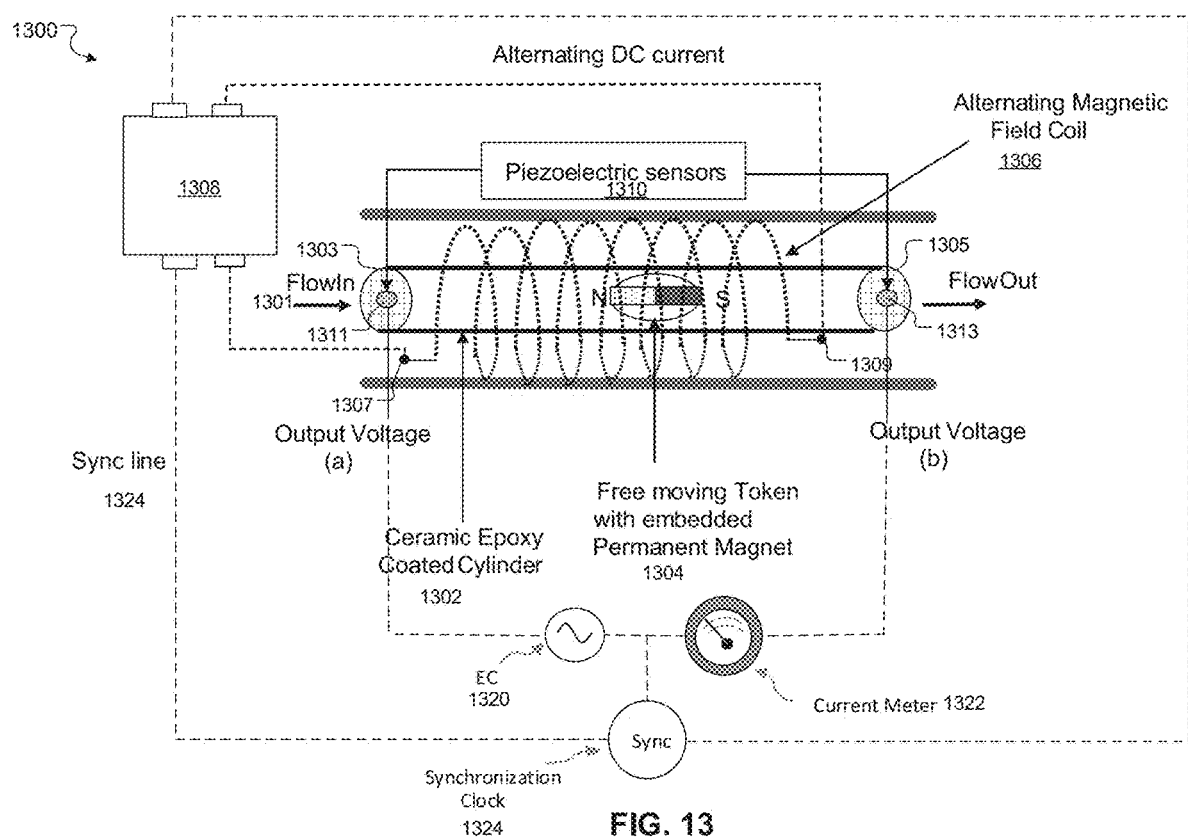
FIG. 13 is a schematic diagram of an example alternating magnetic field flow characterization device using a piezoelectric sensor for salinity measurement according to the present disclosure.

FIG. 13 is a schematic diagram of an example alternating magnetic field flow characterization device 1300 as an RTU. In addition to fluid flow measurements, the alternating magnetic field flow characterization device 1300 provides quality assurance and control by using the same equipment used to that is also used to provide flow measurements.

The alternating magnetic field flow characterization device 1300 is similar to flow meter 100 described with respect to FIG. 1, including many similar components. In brief, a fluid flow 1301 can flow through the conduit 1302 from an inlet 1303 to an outlet 1305, and the conduit 1302 can guide the fluid flow along a flow path. A direction of the flow path can be substantially parallel to the longitudinal direction of the conduit 1302. The alternating magnetic field flow characterization device 1300 includes a conduit 1302, a magnetic token 1304, an electromagnetic coil 1306 as a magnetic field generator, and a piezoelectric sensor 1310 as a detector. The electromagnetic coil 1306 is configured to receive current from a power source 1308 and generate a magnetic field based on the current. The coil 1306 can include a coiled wire having electrical nodes 1307 and 1309 on both ends. The power source 1308 can include an alternating switch relay configured to alternate (or switch) a polarity (or direction) of the current so as to provide an alternating current to the coil 1306. The coil 1306 can then generate an alternating magnetic field based on the alternating current.

The conduit 1302 is arranged within the inner space of the coil 1306 and the direction of the magnetic field generated by the coil 1306 can be also along the longitudinal direction. By changing a direction of the current into the coil 1306, the generated magnetic field can have the same direction as the flow path or a reversed direction against the flow path.

The magnetic token 1304 is movable within the conduit 1302. The magnetic token 1304 can have polar sides "N" and "S." The magnetic token 1304 can be moved by the magnetic field generated by the coil 1306 and by the fluid flow. The coil 1306 can be configured to generate a first magnetic field to move the magnetic token 1304 along the direction of the flow path and generate a second magnetic field to move the magnetic token 1304 opposite to the direction of the flow path. The alternating magnetic flow characterization device 1300 can include a detector configured to detect a first electrical signal associated with the movement of the magnetic token 1304 along the direction of the flow path, and a second electrical signal associated with the movement of the magnetic token 1304 opposite to the direction of the flow path. The alternating magnetic field flow characterization device 1300 can further include a processor configured to determine a flow rate of the fluid flow based on the detected first electrical signal and the detected second electrical signal.

A piezoelectric sensor 1310 can be used as the detector to detect the electrical signals associated with the movement of the magnetic token 1304. The piezoelectric sensor 1310 can include a first surface 1311 coupled to the inlet 1303 of the conduit 1302 and a second surface 1313 coupled to the outlet 1305 of the conduit 1302. When the magnetic token 1304 moves with a velocity to the inlet 1303 or the outlet 1305, the magnetic token 1304 hits the first surface 1311 or the second surface 1313 with a mechanical force to deform the first surface 1311 or the second surface 1313. The piezoelectric sensor 1310 is configured to detect a first voltage signal, for example, output voltage (b) in FIG. 13, when the magnetic token 1304 is moved to deform the second surface 1313 along the direction of the flow path and detect a second voltage signal, for example, output voltage (a) in FIG. 13, when the magnetic token 1304 is moved to deform the first surface 1311 opposite to the direction of the flow path. The flow rate of the fluid flow 1302 can then be determined based on the first voltage signal and the second voltage signal.

The coil 1306 can be configured to alternately generate the first magnetic field and the second magnetic field for a number of times to move the magnetic token along the direction of the flow path of the fluid flow 1301 and against the direction of the flow path of the fluid flow for the number of times. The piezoelectric sensor 1310 can detect a plurality of first voltage signals and a plurality of corresponding second electrical signals when the magnetic token 1304 is moved within the conduit 1302 by the alternating first magnetic field and second magnetic field. Accordingly, the processor can determine the flow rate of the fluid flow 1301 based on respective differences between the first electrical signals and corresponding second electrical signals.

The alternating magnetic field flow characterization device 1300 permits both flow and TDS measurements using this same hardware as described with respect to FIG. 1, with some additions. These additions include an electric charge emitter (EC) 1320 that is an alternating current source, a current meter 1322, and a synchronization clock 1324 that is connected to the power source 1308 via a sync line 1324. The EC 1320 and the current meter 1322 are electrically coupled to the piezoelectric sensors 1310 at the inlet 1303 of the conduit 1302 and at the outlet 1305 of the conduit 1302.

The salinity function of the alternating magnetic field flow characterization device 1300 generates a current with the EC 1320 that travels through the fluid flow 1301 along or against the direction of the flow path. The piezoelectric sensor 1310 acts as a pair of electrodes for the current meter 1322 to measure the resulting current that travels along the conduit 1302, which is affected by the dissolved salts within the fluid flow 1301. Measuring the signal detected by the current meter 1322 gives a conductivity measurement of the fluid flow 1301. The conductivity measurement is directly related to the TDS, which enables determination of the salinity index of the fluid flow 1301.

These TDS measurements occur at times between the alternating magnetic fluxes for the fluid flow measurements. The synchronization clock 1324 coordinates these synchronous electrical input/output process and assigns each process a specific action in accordance with a time slot (t) and a priority (p) factor. The synchronization clock 1324 regulates the dual function of the meter (flow measurement vs TDS measurement) using time and priority indices. Table 2 below shows examples of processes, actions, and priorities assigned with exemplary time slots.

TABLE 2

| Time slot (t) | Process ID (i) | Action (a) | Action (n) | Priority (p) |
|---|---|---|---|---|
| 000.000.001 | Energize Coil | Select current magnitude | Select polarity | (p 1) |
| 000.010.000 | Energize TDS | Select current magnitude | Measure current magnitude | (p 2) |
| 010.010.000 | De-Energize Coil | Measure current magnitude from PE sensors | Determine Flow measurement | (p (n)) |

Figure 14:
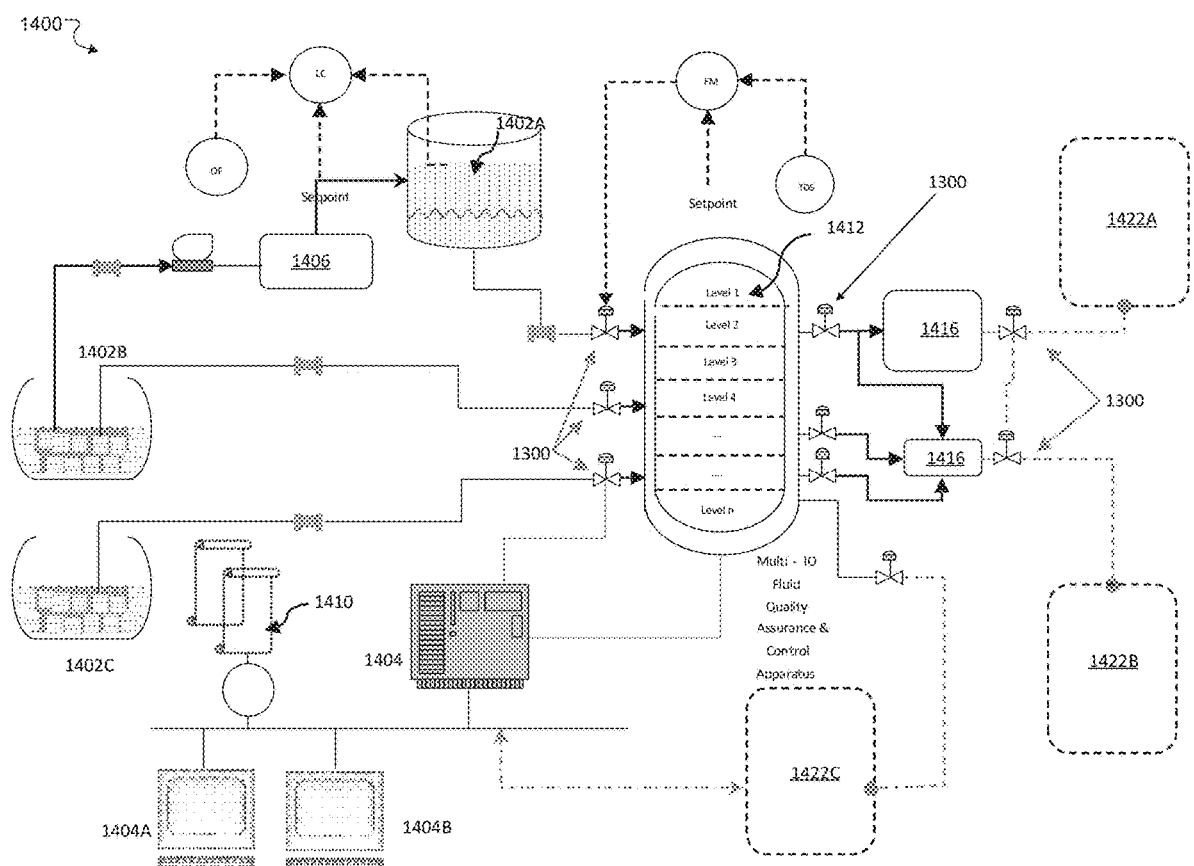
FIG. 14 is schematic diagram of a fluid quality assurance and control system using alternating magnetic field flow characterization devices as shown in FIG. 13.

FIG. 14 shows a system 1400 for controlling and manipulating reservoirs of fluid while assuring fluid quality, for example, a SCADA. The system 1400 includes a network of magnetic field flow characterization devices 1300 that can be used to determine the salinity of multiple reservoirs, such as reservoirs 1402A, 1402B, 1402C. Each of the reservoirs 1402A, 1402B, 1402C can have a different salinity level, for example reservoir 1402A may have no salt, reservoir 1402B some amount of salt (which can be used to feed reservoir 1402A via a de-salter 1406), and a higher salinity reservoir 1402C. While three reservoirs are shown, fewer or more reservoirs are possible. The system can combine fluids from the various reservoirs, for example, into a multi-level tank 1412. Each level of the multi-level tank 1412 can have a different salinity, up to "n" levels. In some instances, there may be a gradient in salinity from the bottom to the top of the multi-level tank 1412.

Fluid in the multi-level tank 1412 can be destined for differing final applications requiring different salinity levels, for example, applications 1422A, 1422B, 1422C. The fluid mixed and removed from the multi-level tank can be characterized by additional magnetic field flow characterization devices 1300, and if necessary, further conditioned by various equipment 1416 before being directed to a respective application 1422A, 1422B, 1422C.

Each of the magnetic field flow characterization devices 1300 can be connected (for example, wired or wirelessly) so as to communicate with the other magnetic field flow characterization devices 1300 in the system 1400. Each magnetic field flow characterization device 1300 can thus receive information about the conductivity measurements determined by other flow meters in the network. Using this information, the magnetic field flow characterization devices 1300 can modify their conductivity measurements of their respective flow conduits, using, for example, methods similar to calibrating flow measurements described above.

A controller 1404 can be used to control and measure the entire system 1400. The controller 1404 can have multiple components or user interfaces, such as processors 1404A and 1404B. The controller 1404 is in communication with a memory or database 1410.

The controller 1404 can obtain an overall community salinity factor for the system 1400 based on a distributed TDS reading output for each magnetic field flow characterization device 1300. In some implementations, the controller 1404 can control the magnetic field flow characterization devices 1300 to generate an individual (for example, pertaining to a specific fluid reservoir 1402 or flowmeter 1300 attached to a reservoir 1300) salinity factor based on an accumulated pattern for each reservoir 1402 or flowmeter 1300 over a period of time. Such measurements can be stored, for example in the memory 1410. The community or individual salinity factor(s) can be used to generate dynamic trends which can be used as input parameters as part of enhanced control system scheme to maximize output by minimizing time-sensitive mixing and quality assurance procedures.

In some implementations, the salinity factor is obtained to determine additional fluid approximate properties such as its density and temperature. Fluid density can be estimated by correlating coefficients of thermal expansion and saline contraction in relationship with temperature, salinity, and pressure figures. Because each magnetic field flow characterization device 1300 is equipped with a networking module and an industrial communication protocol stack, it can easily obtain pressure figures form downstream or upstream pressure sensors.

Figure 15:
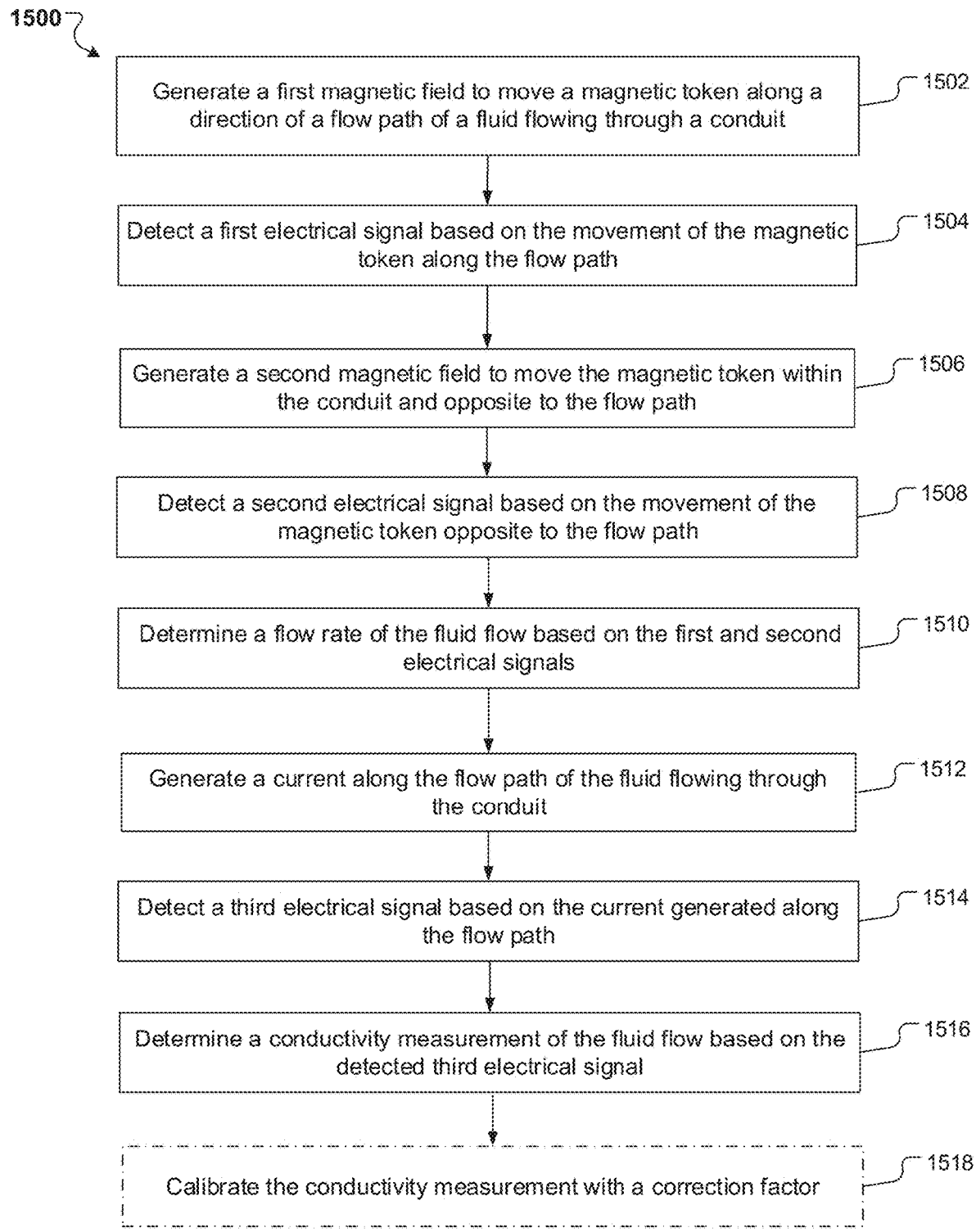
FIG. 15 is a flowchart of an example process of measuring a flow rate and a salinity level of a fluid flow using an alternating magnetic field flow meter according to the present disclosure.

FIG. 15 shows a flowchart of an example process of measuring a flow rate and a salinity level of a fluid flow using an alternating magnetic field flow meter according to the present disclosure. A first magnetic field is generated to move the magnetic token along a direction of the flow path of the fluid flow (1502). The alternating magnetic field flow meter can include an electromagnetic coil, for example, the coil 106 of FIG. 1, configured to generate the first magnetic field based on an input current.

A first electrical signal is detected based on the movement of the magnetic token along the flow path (1504). In some implementations, the flow meter includes a piezoelectric sensor, for example, the piezoelectric sensor 1310 of FIG. 13. The first electrical signal can be detected by detecting a first voltage signal when the magnetic token is moved to deform a first surface of the piezoelectric sensor coupled to an outlet of the conduit. After the coil generates the first magnetic field for a first period of time, the first magnetic field is de-energized by stopping to provide a current to the coil, such that the magnetic token moves in the coil without the first magnetic field and along the direction of flow path to generate a first current signal.

A second magnetic field is generated to move the magnetic token within the conduit and opposite to the direction of the flow path of the fluid flow (1506). The second magnetic field can be generated by reversing a polarity of the current into the electromagnetic coil.

A second electrical signal is detected based on the movement of the magnetic token opposite to the direction of the flow path (1508). In some implementations, the second electrical signal is detected by detecting a second voltage signal when the magnetic token is moved to deform a second surface of the piezoelectric sensor coupled to an inlet of the conduit. In some implementations, after the coil generates the second magnetic field for a second period of time, the second magnetic field is de-energized by stopping to provide the reversed current to the electromagnetic coil, such that the magnetic token moves in the electromagnetic coil without the second magnetic field and opposite to the direction of flow path to generate a second current signal.

A flow rate of the fluid flow is determined based on the first and second electrical signals (1510). In some implementations, the flow rate is determined based on the first and second voltage signals detected by the piezoelectric sensor.

A charge emitter generates a current along the flow path of the fluid flowing through the conduit using (1512). A current meter detects a resulting electrical signal based on the current generated along the flow path (1514). A conductivity measurement of the fluid flow based on the detected third electrical signal is determined (1516).

Associations can be pre-determined based on a number of measurements of relationships between detected currents and the conductivity measurement of the fluid flows. Associations can also be pre-determined based on a number of measurements of relationships between detected currents, conductivity measurement, and the TDS or salinity index of the fluid flows. In some examples, variant measurements are used to create a representative model. The model can be analyzed and correlated against a predicted laboratory prepared scheme to determine the TDS or salinity index of the fluid. For example, fluid flows with known TDS can be used, and corresponding current signals measured. Thus, the model can yield a predictive TDS or salinity index based on a corresponding current reading measured by the device 1300 when a fluid flow flows through the conduit 102 with an unknown TDS or salinity. The model can be updated with additional data over time.

In some examples, the flow meter repeats steps 1502 through 1508 for a number of times.

Optionally, the conductivity measurement can be calibrated with a correction factor (1518). In some examples, when contaminants in the fluid flow follow an even distribution pattern, for example, determined by measurement, the correction factor is determined based on calibration information including contaminants known with even distribution patterns and corresponding correction factors. The device 1300 can receive the calibration information from a calibration lab, for example, a calibration lab similar to the calibration lab 1010 of FIG. 10. In some examples, when contaminants in the fluid flow follow an uneven distribution pattern, the flow meter can use a neural network logic to predict the contaminant distribution pattern for the fluid flow and generate the correction factor based on the predicted contaminant distribution pattern and accumulated calibration information including contaminant distribution patterns and associated accuracy variances of conductivity meters.

What is claimed is:

1. A method of characterizing a fluid flow by an alternating magnetic field flow meter, the method comprising:
    determining a flow rate of a fluid flowing through a conduit by:
        generating a first magnetic field to move a magnetic token along a direction of a flow path of a fluid flowing through a conduit;
        detecting a first electrical signal based on the movement of the magnetic token along the direction of the flow path;
        generating a second magnetic field to move the magnetic token opposite to the direction of the flow path;
        detecting a second electrical signal based on the movement of the magnetic token opposite to the direction of the flow path; and
        determining the flow rate of the fluid flow based on the detected first electrical signal and the detected second electrical signal, and
    determining a conductivity of the fluid flowing through the conduit by:
        generating a current along the flow path of the fluid flowing through the conduit;
        detecting a third electrical signal based on the current generated along the flow path; and
        determining a conductivity measurement of the fluid flow based on the detected third electrical signal.

2. The method of claim 1, further comprising:
    after generating the first magnetic field for a first period of time, de-energizing the first magnetic field;
    after generating the second magnetic field for a second period of time, de-energizing the second magnetic field; and
    after generating the current for a third period of time, de-energizing a charge emitter generating the current.

3. The method of claim 1, comprising:
    sequentially generating the first magnetic field, the second magnetic field, and the current;
    detecting a plurality of first electrical signals, a plurality of corresponding second electrical signals, and a plurality of third electrical signals; and
    synchronizing determination of the flow rate of the fluid flow based on respective differences between the first electrical signals and corresponding second electrical signals and the conductivity measurement based on the plurality of third signals.

4. The method of claim 1, wherein the conductivity measurement is a total dissolved solids level.

5. The method of claim 1, further comprising obtaining a salinity factor based on the third electrical signal.

6. The method of claim 5, further comprising determining additional fluid properties based on the salinity factor.

7. The method of claim 6, wherein the fluid properties are fluid density and temperature.

8. A method of characterizing fluid flows by a network of alternating magnetic field flow meters, the method comprising:
    at each flow meter, determining a flow rate of a fluid flowing through a respective conduit by:
        generating a first magnetic field to move a magnetic token along a direction of a flow path of a fluid flowing through the respective conduit;
        detecting a first electrical signal based on the movement of the magnetic token along the direction of the flow path;
        generating a second magnetic field to move the magnetic token opposite to the direction of the flow path;
        detecting a second electrical signal based on the movement of the magnetic token opposite to the direction of the flow path; and
        determining the flow rate of the fluid flow based on the detected first electrical signal and the detected second electrical signal,
    at each flow meter, determining a conductivity of the fluid flowing through the respective conduit by:
        generating a current along the flow path of the fluid flowing through the conduit;
        detecting a third electrical signal based on the current generated along the flow path; and
        determining a conductivity measurement of the fluid flow based on the detected third electrical signal,
    receiving, at a first flow meter, information about the conductivity measurement determined by a second flow meter in the network, and
    modifying the conductivity measurement of the first flow meter using the received information.

9. The method of claim 8, further comprising:
    determining a plurality of conductivity measurements over time for one of the flow meters on the network, storing the plurality of conductivity measurements, and generating a salinity factor for the flow meter based on the plurality of conductivity measurements.

10. The method of claim 8, further comprising generating trend data based on the conductivity measurements.

11. The method of claim 8, further comprising:
after generating the first magnetic field for a first period of time, de-energizing the first magnetic field;
after generating the second magnetic field for a second period of time, de-energizing the second magnetic field; and
after generating the current for a third period of time, de-energizing a charge emitter generating the current.

12. The method of claim 8, comprising:
sequentially generating the first magnetic field, the second magnetic field, and the current;
detecting a plurality of first electrical signals, a plurality of corresponding second electrical signals, and a plurality of third electrical signals; and
synchronizing determination of the flow rate of the fluid flow based on respective differences between the first electrical signals and corresponding second electrical signals and the conductivity measurement based on the plurality of third signals.

13. The method of claim 8, wherein the conductivity measurement is a total dissolved salts level.

14. The method of claim 8, further comprising obtaining a salinity factor based on the third electrical signal.

15. The method of claim 14, further comprising determining additional fluid properties based on the salinity factor.

16. The method of claim 15, wherein the fluid properties are fluid density and temperature.

17. An alternating magnetic field flow apparatus comprising:
a magnetic token movable within a conduit configured to guide a hydrocarbon flow along a flow path;
a magnetic field generator configured to generate alternating magnetic fields within the conduit to move the magnetic token along the flow path with a first flow velocity and opposite to the flow path with a second flow velocity;
a detector configured to measure respective first and second electrical signals responsive to the alternating magnetic fields, the first and second electrical signals associated with the first and second flow velocities;
a charge emitter configured to generate a current along the flow path of the fluid flowing through the conduit;
a current meter configured to measure current signals resulting from generating the current along the flow path; and
a processor configured to determine a flow rate of the hydrocarbon flow based on the first and second electrical signals and determine a salinity factor of the hydrocarbon flow based on the current signals.

18. The alternating magnetic field flow apparatus of claim 17, further comprising a communication module configured to communicate salinity factor information with one or more other flow meters via inter-meter communication, wherein the processor is configured to modify the salinity factor based on the salinity factor information from the one or more other flow meters.

19. The alternating magnetic field flow apparatus of claim 17, wherein the apparatus comprises a piezoelectric sensor including a first surface coupled to an inlet of the conduit and a second surface coupled to an outlet of the conduit that are configured to act as electrodes for measuring the current signals.

20. The alternating magnetic field flow apparatus of claim 19, wherein the detector is configured to:
detect a first voltage signal when the magnetic token is moved to deform the second surface along the direction of the flow path, the first electrical signal including the first voltage signal; and
detect a second voltage signal when the magnetic token is moved to deform the first surface opposite to the direction of the flow path, the second electrical signal including the second voltage signal.

21. The alternating magnetic field flow apparatus of claim 17, further comprising a synchronization clock configured to control the magnetic field generator to generate the alternating magnetic fields at different times (for flow measurement) than it controls the charge emitter to generate the current (for quality assessment).

22. The alternating magnetic field flow apparatus of claim 17, wherein the salinity factor is a measurement of a total dissolved solids level in the fluid.

23. The alternating magnetic field flow apparatus of claim 17, wherein the salinity factor is determined by a conductivity measurement based on the current signals.

* * * * *